United States Patent
Guido et al.

(10) Patent No.: US 9,517,208 B2
(45) Date of Patent: Dec. 13, 2016

(54) ABUSE-DETERRENT DOSAGE FORMS

(71) Applicant: PURDUE PHARMA L.P., Stamford, CT (US)

(72) Inventors: Debora L Guido, Bordentown, NJ (US); Haiyong Huang, Princeton, NJ (US)

(73) Assignee: Purdue Pharma L.P., Stamford, CT (US)

(*) Notice: Subject to any disclaimer, the term of this patent is extended or adjusted under 35 U.S.C. 154(b) by 46 days.

(21) Appl. No.: 14/207,826

(22) Filed: Mar. 13, 2014

(65) Prior Publication Data

US 2014/0271848 A1   Sep. 18, 2014

Related U.S. Application Data

(60) Provisional application No. 61/793,684, filed on Mar. 15, 2013.

(51) Int. Cl.
| | | |
|---|---|---|
| *A61K 31/485* | (2006.01) | |
| *A61K 9/20* | (2006.01) | |
| *A61K 45/06* | (2006.01) | |
| *A61K 9/28* | (2006.01) | |

(52) U.S. Cl.
CPC ............... *A61K 9/28* (2013.01); *A61K 9/2009* (2013.01); *A61K 9/2018* (2013.01); *A61K 9/2031* (2013.01); *A61K 9/2054* (2013.01); *A61K 31/485* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 3,980,766 A | 9/1976 | Shaw et al. | |
| 5,866,164 A | 2/1999 | Kuczynski et al. | |
| 6,696,066 B2 | 2/2004 | Kaiko et al. | |
| 6,696,088 B2 | 2/2004 | Oshlack et al. | |
| 7,144,587 B2 | 12/2006 | Oshlack et al. | |
| 7,332,182 B2 | 2/2008 | Sackler et al. | |
| 7,727,557 B2 | 6/2010 | Sackler | |
| 7,842,307 B2 | 11/2010 | Oshlack et al. | |
| 8,017,148 B2 | 9/2011 | Sackler | |
| 8,652,497 B2 | 2/2014 | Sackler | |
| 8,652,515 B2 | 2/2014 | Sackler | |
| 2003/0064122 A1 | 4/2003 | Goldberg | |
| 2003/0068375 A1 | 4/2003 | Wright et al. | |
| 2003/0191147 A1* | 10/2003 | Sherman et al. | 514/282 |
| 2007/0231268 A1 | 10/2007 | Emigh et al. | |
| 2008/0020039 A1* | 1/2008 | Parikh et al. | 424/472 |
| 2011/0054038 A1 | 3/2011 | Glozman | |
| 2013/0178492 A1* | 7/2013 | Danagher | A61K 9/1676 514/282 |

OTHER PUBLICATIONS

"Sugar Spheres—2012 Indiamart" [downloaded on Aug. 17, 2015 from the website http://www.cornileus.com/polymer.html].*
The Advanced Osmometer Model 3250 User's Guide, Advanced Instruments, Inc., 2003.
"OxyNorm 10 mg/ml solution for injection or infusion"—SPS—EMC. Obtained from http://www.medicines.org/uk/emc/medicine/12151_.on Nov. 16, 2011.
Roxicodone (Oxycodone Hydrochloride Tables USP) Xanodyne Pharmaceuticals, Inc., Revised Mar. 2011.
Steinbrocker et al., "Observations on pain produced by injection of Hypertonic Saline into muscles and other", 1952.
"Tonicity, Osmoticity, Osmolality and Osmolarity", Remington, pp. 250-259, 2005.
e-CFR data color additives, Dec. 12, 2011.

* cited by examiner

*Primary Examiner* — Sue Liu
*Assistant Examiner* — Thor Nielsen
(74) *Attorney, Agent, or Firm* — Davidson, Davidson & Kappel, LLC

(57) ABSTRACT

Abuse-deterrent dosage forms (e.g., orally administered dosage forms, transdermal dosage forms, suppositories, etc.), processes for formulating pharmaceutical dosage forms comprising an active agent susceptible to abuse (e.g., an opioid agonist, a benzodiazepine, a stimulant) such that the resulting dosage forms are abuse-deterrent are described. Also described are methods of deterring abuse of pharmaceutical dosage forms.

8 Claims, No Drawings

ABUSE-DETERRENT DOSAGE FORMS

This application claims the benefit of U.S. Provisional Application No. 61/793,684, filed on Mar. 15, 2013, which is hereby incorporated by reference.

BACKGROUND OF THE INVENTION

Pharmaceutical dosage forms containing opioid analgesics, benzodiazepines, barbiturates, and stimulants are subject to abuse in a variety of ways.

With oral solid dosage forms containing these active agents, drug abusers may crush oral solid dosage forms to powders and/or extract the active agents from the dosage forms and then self-administer the extracted active agents by injection, intranasaly or by inhalation (e.g., by snorting). Abusers may also self-administer more than one dose at a time, either orally or by injection. Typically, abusers dissolve the crushed dosage form in from about 2 ml to about 5 ml of a solvent (e.g., water) and then inject the resulting solution, suspension or gel intravenously.

With transdermal dosage forms (e.g., transdermal patches) containing these active agents, abusers may freeze transdermal dosage forms, cut them into pieces and then place one or more pieces inside their oral cavities for intraoral (i.e., buccal) administration. Alternatively, abusers may place a transdermal dosage form in a solvent to extract the active agent and then self-administer the extracted active agent either orally or by injection.

Various attempts have been made to develop abuse-deterrent dosage forms. Despite such attempts, the misuse and abuse of pharmaceutical dosage forms continue to increase.

Thus, there remains a need for new abuse-deterrent pharmaceutical dosage forms and methods for deterring abuse.

SUMMARY OF THE INVENTION

The present invention is directed in part to abuse-deterrent pharmaceutical dosage forms (e.g., orally administered dosage forms, transdermal dosage forms, suppositories, etc.), processes for formulating pharmaceutical dosage forms comprising an active agent susceptible to abuse (e.g., opioid agonists, benzodiazepines, barbiturates, stimulants, etc.) such that the resulting dosage forms are abuse-deterrent, and methods of using such pharmaceutical dosage forms to treat certain conditions.

The dosage forms of the present invention comprise tonicity-increasing agents in effective amounts to deter abuse of the dosage forms by forming hypertonic solutions, suspensions or gels upon contact of the dosage forms with one or more solvents, or, when a transdermal dosage form or a crushed oral solid dosage form, contacts an oral and/or nasal mucosal membrane of a subject (e.g., a human intending to abuse the dosage form), the hypertonic solutions, suspensions or gels having an osmolality sufficient to cause pain and/or burning at the contact site or, when the hypertonic solution, suspension or gel is administered by an injection (e.g., by an intravenous injection), at the injection site. The pain and burning is preferably of the intensity and duration sufficient to deter abuse of the dosage forms.

An amount of the tonicity-increasing agent(s) in the dosage form of the present invention is specific to a particular dosage form and will vary between dosage forms comprising different components or the same components but in different amounts. The osmolality of the resulting solution, suspension or gel sufficient to cause pain and burning sufficient to deter abuse of the dosage form is typically from about 380 mOsmol/L to about 10000 mOsmol/L, from about 380 mOsmol/L to about 5000 mOsmol/L, from about 380 mOsmol/L to about 2500 mOsmol/L, from about 380 mOsmol/L to about 880 mOsmol/L, or from about 1000 mOsmol/L to 2500 mOsmol/L. In some of the preferred embodiments, the osmolality which causes pain and burning sufficient to deter abuse of the dosage form is from about 1000 mOsmol/L to 2500 mOsmol/L. The pH of the resulting solutions, suspensions or gels may, e.g., be from about 5.5 to about 8, from about 6 to about 7.8, from about 6 to about 7.5, from about 6.5 to about 7.5, or from about 7 to about 7.5. In some of these embodiments, pH is from about 6.5 to about 7.5.

Hypertonic solutions, suspensions and gels prepared from an abuse-deterrent pharmaceutical dosage form of the invention may cause pain or burning at a site in the subject where the solution, suspension or gel has been injected intravenously.

Hypertonic solutions, suspensions and gels prepared from an abuse-deterrent pharmaceutical dosage form of the invention may cause pain or burning if contacted with nasal mucosal membranes. Such would be the case if such a solution, suspension or gel was snorted or sprayed into the nose by an abuser.

Hypertonic solutions, suspensions and gels prepared from an abuse-deterrent pharmaceutical dosage form of the invention may cause pain or burning if contacted with mucosal membranes of the mouth or esophagus if taken by the oral route. Furthermore, if an abuser attempts to consume a dose that exceeds the dose recommended by the manufacturer, in certain embodiments, the hypertonic solutions, suspensions or gels prepared from an abuse-deterrent pharmaceutical dosage form of the present invention or formed when the dose that exceeds the dose recommended by the manufacturer is exposed to gastrointestinal fluids may cause GI irritation, diarrhea and/or increased urination in the abuser.

The abuser is therefore likely to experience an unpleasant sensation (e.g., pain or burning at the administration site) whenever the abuser administers the dosage form contrary to the directions or route of administration recommended by the manufacturer, and, with time, is likely to associate the dosage form and/or the mode of administration with the unpleasant sensation.

Once the abuser associates the discomfort with the dosage form or the route of administration of the dosage form, the abuser would then be less likely to abuse the dosage form. A dosage form in accordance with the present invention therefore has a lower abuse potential than an identical dosage form which does not comprise a tonicity-increasing agent or comprises an amount of the tonicity-increasing agent which is lower than the amount of the tonicity-increasing agent contemplated by the present invention.

It should be understood that the amount of the tonicity-increasing agent absorbed into the systemic circulation from the dosage form of the present invention, which is administered contrary to the directions or route of administration recommended by the manufacturer, will only cause local pain or burning (i.e., at the administration site or the contact site), and will be insufficient to raise the serum osmolality in the abuser above 330 mOsmol/L, based on normal serum osmolality being 285 mOsmol/L. A rise in serum osmolality above 330 mOsmol/L is likely to be associated with potential negative systemic effects of the tonicity-increasing agent (e.g., weakness, disorientation, postural hypotension, fainting, CNS changes and coma). A rise in serum osmolality above 330 mOsmol/L should therefore be avoided by the methods and dosage forms of the present invention. The amount of the tonicity-increasing agent absorbed into the systemic circulation from the dosage forms of the present invention is intended to be insufficient to cause negative systemic effects of the tonicity-increasing agent.

In general, the amount of the tonicity-increasing agent in the dosage form is such that a dosage form, when dissolved in 10 ml, preferably from about 2 ml to about 5 ml, of distilled water, will provide a solution, suspension or gel having an osmolality of from about 300 mOsmol/L to about 126000 mOsmol/L, or from about 320 mOsmol/L to about 100000 mOsmol/L, or from about 320 mOsmol/L to about 80000 mOsmol/L, or from about 340 mOsmol/L to about 80000 mOsmol/L. In certain embodiments, the osmolality of the hypertonic solution is from about 300 mOsmol/L to about 9000 mOsmol/L. In certain embodiments, the osmolality of the hypertonic solution is from about 120000 mOsmol/L to about 125600 mOsmol/L. Because each component of the dosage form has a potential to contribute to the tonicity of the resulting solution, suspension or gel, dosage forms containing different components, or the same components but in different amounts, will contain different amounts of tonicity-increasing agents.

The exact amount of the tonicity increasing agent to be included in a particular dosage form according to the present invention may be determined as described herein below. In the preferred embodiments, the osmolality of the resulting solution, suspension or gel is typically such that, when the dosage form is dissolved in from about 2 ml to about 5 ml of water (e.g., distilled water) and injected (e.g., intravenously) into a subject or is crushed and contacted with a nasal or mucosal membrane of the subject, the subject will experience pain and/or burning sufficient for the subject to associate the pain and/or burning with the mode of administration of the dosage form and deter the subject from administering the dosage form by intravenous injection, buccally and/or by snorting. In these embodiments, the osmolality of the resulting solution, suspension or gel may be from about 380 mOsmol/L to about 10000 mOsmol/L, from about 380 mOsmol/L to about 5000 mOsmol/L, from about 380 mOsmol/L to about 2500 mOsmol/L, from about 380 mOsmol/L to about 880 mOsmol/L, or from about 1000 mOsmol/L to about 2500 mOsmol/L. In the most preferred embodiments, the osmolality is from about 1000 mOsmol/L to about 2500 mOsmol/L.

The present invention further encompasses the use of the tonicity-increasing agent alone, or in combination with one or more additional abuse-deterrent agents (e.g., gelling agents, irritants, bittering agents, surfactants, staining agents, laxatives, pharmacological antagonists of active agents, etc.) in preparing abuse-deterrent dosage forms.

In certain embodiments, an abuse-deterrent dosage form of the present invention comprises a therapeutically effective amount of an active agent susceptible to abuse and one or more tonicity-increasing agent(s), wherein the tonicity-increasing agent is in an effective amount to provide a hypertonic solution, suspension or gel of the active agent upon dissolution of the dosage form in 10 ml distilled water which is sufficiently hypertonic to deter abuse.

In certain embodiments, an abuse-deterrent dosage form of the present invention comprises a therapeutically effective amount of an active agent susceptible to abuse, and a tonicity-increasing agent, wherein the tonicity-increasing agent is in an effective amount to provide a hypertonic solution, suspension or gel having an osmolality of from about 300 mOsmol/L to about 80,000 mOsmol/L, from about 380 mOsmol/L to about 10000 mOsmol/L, or from about 800 mOsmol/L to about 25000 mOsmol/L upon dissolution of the dosage form in 10 ml, preferably in from about 2 ml to about 5 ml, of solvent of a type used by addicts attempting to abuse dosage forms comprising such active agents. In the preferred embodiments, these osmolalities case pain and/or burning at the injection site sufficient to deter abuse of the dosage form. In some of these embodiments, the abuse-deterrent dosage form is an oral, solid dosage form.

In certain embodiments, an abuse-deterrent dosage form comprises an opioid agonist and a tonicity-increasing agent, wherein the tonicity-increasing agent is in an effective amount to provide a hypertonic solution, suspension or gel of the opioid agonist upon dissolution of the dosage form in 10 ml, preferably in from about 2 ml to about 5 ml, of solvent, and the opioid agonist is in an effective amount to produce analgesia in a subject (e.g., a human). In the preferred embodiments, the hypertonic solution, suspension or gel is sufficiently hypertonic to deter abuse of the dosage form. In some of these embodiments, the abuse-deterrent dosage form is an oral, solid dosage form.

In certain embodiments, an abuse-deterrent oral, solid dosage form comprises an active agent susceptible to abuse and a tonicity-increasing agent, wherein the tonicity-increasing agent is in an effective amount to provide a hypertonic solution upon dissolution of the dosage form in 10 ml, preferably from about 2 ml to about 5 ml, of a solvent. In certain embodiments, the osmolality of the hypertonic solution is from about 300 mOsmol/L to about 5000 mOsmol/L, from about 380 mOsmol/L to about 10000 mOsmol/L or from about 800 mOsmol/L to about 25000 mOsmol/L, and the drug susceptible to abuse is in an effective amount to produce a therapeutic effect (e.g., analgesia).

In certain embodiments, an abuse-deterrent oral solid dosage form of the present invention may comprise an active agent susceptible to abuse and a tonicity-increasing agent, wherein the tonicity-increasing agent is in an effective amount to provide a hypertonic solution, suspension or gel of the active agent upon dissolution of the dosage form, wherein an osmolality the hypertonic solution, suspension or gel is from about 450 mOsmol/L to about 10000 mOsmol/L and is sufficiently hypertonic to deter abuse.

In additional embodiments, an abuse-deterrent oral, solid dosage form is an abuse-deterrent oral solid dosage form comprising an active agent susceptible to abuse and a tonicity-increasing agent, wherein the tonicity-increasing agent is in an effective amount to provide a hypertonic solution, suspension or gel of the active agent upon dissolution of the dosage form in 10 ml of distilled water, the solution, suspension or gel is sufficiently hypertonic to deter abuse, and the drug susceptible to abuse is in an effective amount to produce a therapeutic effect.

In additional embodiments, an abuse-deterrent oral solid dosage form comprises an active agent susceptible to abuse and a tonicity-increasing agent, wherein the tonicity-increasing agent is in an effective amount to provide a hypertonic solution, suspension or gel of the active agent upon contact of the tampered dosage form with a nasal or oral mucosal membrane, wherein an osmolality the hypertonic solution, suspension or gel is from about 380 mOsmol/L to about 10000 mOsmol/L and is sufficiently hypertonic to deter abuse.

In further embodiments, an abuse-deterrent oral solid dosage form comprises an active agent susceptible to abuse and a tonicity-increasing agent, wherein the tonicity-increasing agent is in an effective amount to provide a hypertonic solution, suspension or gel of the active agent and cause pain or burning upon contact of the tampered dosage form with a nasal or oral mucosal membrane of a mammal, and the drug susceptible to abuse is in an effective amount to produce a therapeutic effect.

In additional embodiments, an abuse-deterrent oral solid dosage form comprises an active agent susceptible to abuse, a filler, a lubricant and one or more tonicity-increasing agents. In some of these embodiments, the filler is microcrystalline cellulose, the lubricant is magnesium stearate and two tonicity-increasing agents are used (e.g., dextrose and potassium phosphate dibasic or dextrose and sodium chloride), and the active agent susceptible to abuse is an opioid analgesic.

In certain embodiments, an abuse-deterrent oral solid dosage form comprises an active agent susceptible to abuse and a tonicity-increasing agent, wherein the tonicity-increasing agent is in an effective amount to provide a hypertonic solution, suspension or gel of the active agent within 3 seconds, 5 seconds, 10 seconds, 15 seconds, 30 seconds, 45 seconds, 1 minute, 2 minutes, 3 minutes, 5 minutes, 6 minutes, 7 minutes, 8 minutes or 10 minutes from the time of contact of the dosage form with from about 1 to about 10 ml of a solvent (e.g., 2, 3, 5, or 10 ml of the solvent). In the preferred embodiments, the hypertonic solution, suspension or gel is sufficiently hypertonic to deter abuse of the dosage form. In some of these embodiments, the solvent is distilled water.

In additional embodiments, an abuse-deterrent dosage form comprises an active agent susceptible to abuse and a tonicity-increasing agent, wherein the tonicity-increasing agent is in an effective amount to provide a hypertonic solution, suspension or gel of the active agent having a viscosity of from about 1 cP to about 5000000 cP when the dosage form is crushed and mixed with from about 1 ml to about 20 ml of distilled water, more preferably from about 1 ml to about 10 ml of distilled water, e.g., 10 ml, or from 2 ml to 5 ml, of distilled water. In the preferred embodiments, the hypertonic solution, suspension or gel is sufficiently hypertonic to deter abuse of the dosage form. In some of these embodiments, the abuse-deterrent dosage form is an oral, solid dosage form.

In further embodiments, an abuse-deterrent dosage form comprises an active agent susceptible to abuse and a tonicity-increasing agent, wherein the tonicity-increasing agent is in an effective amount to provide a hypertonic solution, suspension or gel of the active agent having a viscosity of less than about 8 cP (e.g., from about 1 cP to about 7 cP) when the dosage form is crushed and mixed with from about 0.5 ml to 10 ml (e.g., 10 ml), or with from about 2 ml to about 5 ml, of the solvent. The osmolality of the hypertonic solution, suspension or gel may be from about 380 mOsmol/L to about 10000 mOsmol/L. In some of these embodiments, the solvent is distilled water, and the abuse-deterrent dosage form is an oral, solid dosage form.

In other embodiments, an abuse-deterrent oral, an abuse-deterrent solid dosage form comprises an active agent susceptible to abuse and a tonicity-increasing agent, wherein the tonicity-increasing agent is in an effective amount to provide a hypertonic solution, suspension or gel of the active agent having a viscosity of from about 1 cP to about 7 cP, when the dosage form is crushed and mixed with 10 ml, or with from about 2 ml to about 10 ml, of the solvent (e.g., distilled water). It is believed that the solution, suspension or gel having a viscosity of from about 1 cP to about 7 cP will not impede the absorption of the active agent from the hypertonic solution, suspension or gel.

In additional embodiments, an abuse-deterrent solid dosage form comprises (i) an active agent susceptible to abuse, (ii) a tonicity-increasing agent in an effective amount to provide a hypertonic solution, suspension or gel of the active agent, when the dosage form is crushed and mixed with from about 2 ml to about 10 ml (e.g., 3 ml) of a solvent (e.g., distilled water) and (iii) PEO, polyvinyl alcohol, hydroxypropyl methylcellulose, or a mixture of any of the foregoing.

In further embodiments, an abuse-deterrent oral, solid dosage form is an oral controlled release dosage form comprising an active agent susceptible to abuse and a plurality of particles comprising a sequestered tonicity-increasing agent, wherein the tonicity-increasing agent is in an effective amount to provide a hypertonic solution, suspension or gel of the active agent upon contact of the crushed dosage form with 10 ml, or with from about 2 ml to about 10 ml, of the solvent (e.g., distilled water), and the drug susceptible to abuse is in an effective amount to produce a therapeutic effect. In these embodiments, the tonicity-increasing agent is formulated with a sequestering material such that the tonicity-increasing agent does not come in contact with the fluid entering the dosage form which is administered (or tested) intact. In some of these embodiments, the abuse-deterrent oral solid dosage form further comprises a releasable tonicity-increasing agent. In the preferred embodiments, the hypertonic solution, suspension or gel is sufficiently hypertonic to deter abuse of the dosage form.

An abuse-deterrent oral solid dosage form of the invention may comprise a core comprising an active agent susceptible to abuse, a tonicity-increasing agent, and one or more pharmaceutically acceptable excipients, wherein the tonicity-increasing agent is in an effective amount to provide a hypertonic solution, suspension or gel of the active agent upon contact of the dosage form with 10 ml, or with from about 2 ml to about 5 ml, of the solvent (e.g., distilled water). The core may provide an immediate release of the active agent (i.e., at least 75% of the active agent is released from an intact dosage form within 1 hour of placing the dosage form in 900 ml of water, as determined by USP 37 Type II dissolution apparatus (Paddle), 75 rpm at 37° C.) or a controlled release of the active agent for at least 6 hours to 24 hours and such that not more than 30% of the active agent is released from an intact dosage form within 1 hour of placing the dosage form in 900 ml of water, as determined by USP 37 Type II dissolution apparatus (Paddle), 75 rpm at 37° C.

In certain embodiments, an abuse-deterrent oral solid dosage form comprises a mini-tablet comprising a drug susceptible to abuse and a tonicity-increasing agent comprising dextrose, mannitol, a sodium salt, a potassium salt, or a mixture of any of the foregoing, wherein the tonicity-increasing agent is in an effective amount to provide a hypertonic solution or suspension of the active agent upon contact of the dosage form with 10 ml, or from about 2 ml to about 5 ml, of a solvent and/or upon the dissolution of the dosage form therein. In some of these embodiments, the sodium salt is sodium chloride or sodium bicarbonate and the potassium salt is potassium phosphate. In the preferred embodiments, the osmolality of the resulting solution or suspension or gel is such that, when from about 2 ml to about 5 ml of the solution or suspension is injected (e.g., intravenously) into a subject, the subject experiences pain and/or burning sufficient for the subject to associate the pain or burning with the injection of the dissolved mini-tablets and deter the subject from injecting the dissolved mini-tablets again.

In additional embodiments, an abuse-deterrent oral solid dosage form comprises a mini-tablet comprising an active agent susceptible to abuse, a tonicity-increasing agent and an agent selected from the group consisting of polyethylene oxides, hydroxymethylalkylcelluloses, hydroxyalkylcelluloses, and mixtures of any of the foregoing, wherein the tonicity-increasing agent is in an effective amount to provide a hypertonic solution, suspension or gel of the active agent upon contact of the dosage form with 10 ml, or with from about 2 ml to about 5 ml, of a solvent and/or upon the dissolution of the dosage form therein. In certain embodiments, the mini-tablet provides an immediate release of the active agent susceptible to abuse (i.e., at least 75% of the active agent is released from the mini-tablet within 1 hour of placing the mini-tablet in 900 ml of water, as determined by USP 37 Type II dissolution apparatus (Paddle), 75 rpm at 37° C.).

In further embodiments, an abuse-deterrent oral solid dosage form comprises a mini-tablet comprising an active agent susceptible to abuse, a tonicity-increasing agent comprising dextrose, mannitol, a sodium salt, a potassium salt, or a mixture of any of the foregoing, and an agent selected from the group consisting of polyethylene oxides, hydroxymethylcelluloses, hydroxypropylmethylcelluloses, and mixtures of any of the foregoing, wherein the tonicity-increasing agent is in an effective amount to provide a hypertonic solution, suspension or gel of the active agent upon contact of the dosage form with 10 ml, or with from about 2 ml to about 5 ml, of a solvent and/or upon the dissolution of the dosage form therein. The solution, suspension or gel is preferably sufficiently hypertonic to deter abuse of the dosage form. The tonicity-increasing agent may comprise from, e.g., about 0.01% to about 90% or from about 0.01% to about 45% or from about of the dosage form by weight.

In certain embodiments, an abuse-deterrent oral solid dosage form comprises a mini-tablet comprising a drug susceptible to abuse, a polyethylene oxide, a flowing agent and a tonicity-increasing agent comprising dextrose, mannitol, a sodium salt, a potassium salt or a mixture of any of the foregoing, wherein the tonicity-increasing agent is in an effective amount to provide a hypertonic solution or suspension of the active agent upon contact of the dosage form with 10 ml, or with from about 2 ml to about 5 ml, of a solvent and/or upon the dissolution of the dosage form therein. The solution or suspension is preferably sufficiently hypertonic to deter abuse of the dosage form. The flowing agent may, e.g., comprise talc, corn starch, microcrystalline cellulose, stearic acid, metallic stearates (e.g., magnesium stearate), silica or a mixture of any of the foregoing.

In additional embodiments, an abuse-deterrent oral solid dosage form comprises a plurality of mini-tablets, each mini-tablet comprising an active agent susceptible to abuse and a tonicity-increasing agent, wherein the tonicity-increasing agent is in an effective amount to provide a hypertonic solution or suspension of the active agent upon contact of the dosage form with 10 ml, or with from about 2 ml to about 5 ml, of a solvent and/or upon the dissolution of the dosage form therein.

In further embodiments, an abuse-deterrent oral solid dosage form comprises a plurality of mini-tablets, each mini-tablet comprising an active agent susceptible to abuse, a tonicity-increasing agent and an agent selected from the group consisting of polyethylene oxides, hydroxymethylalkylcelluloses, hydroxyalkylcelluloses, and mixtures of any of the foregoing, wherein the tonicity-increasing agent is in an effective amount to provide a hypertonic solution, suspension or gel of the active agent upon contact of the dosage form with 10 ml, or with from about 2 ml to about 5 ml, of a solvent and/or upon the dissolution of the dosage form therein.

In certain embodiments, an abuse-deterrent oral solid dosage form comprises a plurality of mini-tablets, each mini-tablet comprising an active agent susceptible to abuse; a tonicity-increasing agent comprising dextrose, mannitol, a sodium salt or a mixture of any of the foregoing; and an agent selected from the group consisting of polyethylene oxides, hydroxymethylcelluloses, hydroxypropylmethylcelluloses, and mixtures of any of the foregoing; wherein the tonicity-increasing agent is in an effective amount to provide a hypertonic solution, suspension or gel of the active agent upon contact of the dosage form with 10 ml or with from about 2 ml to about 5 ml, of a solvent and/or upon the dissolution of the dosage form therein.

In other embodiments, an abuse-deterrent oral solid dosage form comprises a core comprising an active agent susceptible to abuse and a tonicity-increasing agent, and a water-soluble, water-swellable or water-erodable coating coated over the core, wherein the tonicity-increasing agent is in an effective amount to provide a hypertonic solution, suspension or gel of the active agent upon contact of the dosage form with 10 ml, or with from about 2 ml to about 5 ml, of a solvent and/or upon the dissolution of the dosage form therein. The hypertonic solution, suspension or gel is preferably sufficiently hypertonic to deter abuse of the dosage form. In some of these embodiments, the water-soluble coating comprises a hydrophobic material and a hydrophilic material. In the preferred embodiments, the coating coated over the core is not a semi-permeable membrane.

In further embodiments, an abuse-deterrent oral, solid dosage form comprises an active agent susceptible to abuse, a gelling agent (e.g., polyethylene oxide) and a tonicity-increasing agent, wherein, upon placement of the dosage form in from about 2 ml to about 15 ml of distilled water, the active agent susceptible to abuse is released before the gelling agent begins to swell, and the tonicity-increasing agent is in an effective amount to provide a hypertonic solution, suspension or gel within 3 seconds, 5 seconds, 10 seconds, 15 seconds, 30 seconds, 45 seconds, 1 minute, 2 minutes, 3 minutes, 5 minutes, 6 minutes, 7 minutes, 8 minutes or 10 minutes after placement of the dosage form in the water. The hypertonic solution, suspension or gel is preferably sufficiently hypertonic to deter abuse of the dosage form.

In additional embodiments, an abuse-deterrent oral solid dosage form comprises a core comprising a blended mixture of an active agent susceptible to abuse and polyethylene oxide, the core coated with one or more layers, each layer independently comprising (i) a tonicity-increasing agent, (ii) a hydroxypropylmethylcellulose, (iii) a polyethylene glycol, (iv) a mixture of the tonicity-increasing agent and the hydroxypropylmethylcellulose, (v) a mixture of the tonicity-increasing agent and the polyethylene glycol, (vi) a mixture of the tonicity-increasing agent, the hydroxypropylmethylcellulose and the polyethylene glycol, or (vii) a mixture of the hydroxypropylmethylcellulose and the polyethylene glycol, wherein at least one of the layers comprises the tonicity-increasing agent.

In certain embodiments, an abuse-deterrent oral solid dosage form comprises a core comprising a blended mixture of an agent susceptible to abuse, polyethylene oxide, and a flowing agent, the core coated with one or more layers, each layer independently comprising (i) a tonicity-increasing agent, (ii) a hydroxypropylmethylcellulose, (iii) a polyethylene glycol, (iv) a mixture of the tonicity-increasing agent and the hydroxypropylmethylcellulose, (v) a mixture of the tonicity-increasing agent and the polyethylene glycol, (vi) a mixture of the tonicity-increasing agent, the hydroxypropylmethylcellulose and the polyethylene glycol, or (vii) a mixture of the hydroxypropylmethylcellulose and the polyethylene glycol, wherein at least one of the layers comprises the tonicity-increasing agent.

In further embodiments, an abuse-deterrent oral solid dosage form comprises a core comprising a blended mixture of an agent susceptible to abuse, polyethylene oxide, and magnesium stearate, the core coated with one or more layers, each layer independently comprising (i) a tonicity-increasing agent, (ii) a hydroxypropylmethylcellulose, (iii) a polyethylene glycol, (iv) a mixture of the tonicity-increasing agent and the hydroxypropylmethylcellulose, (v) a mixture of the tonicity-increasing agent and the polyethylene glycol, (vi) a mixture of the tonicity-increasing agent, the hydroxypropylmethylcellulose and the polyethylene glycol, or (vii) a mixture of the hydroxypropylmethylcellulose and the polyethylene glycol, wherein at least one of the layers comprises the tonicity-increasing agent.

In additional embodiments, an abuse-deterrent oral solid dosage form comprises a controlled release matrix comprising an active agent susceptible to abuse, a tonicity-increasing agent and a hydrophobic material, wherein the active agent and the tonicity-increasing agent are interspersed in the hydrophobic material and are released from the dosage form at the same or substantially the same rate (i.e., the rates that do not vary from each other by more than 15%), and the tonicity-increasing agent is in an effective amount to provide a hypertonic solution, suspension or gel of the active agent upon contact of the dosage form with 10 ml, or with from about 2 ml to about 5 ml, of a solvent (e.g., distilled water). The osmolality of the hypertonic solution, suspension or gel may be from about 380 mOsmol/L to about 10000 mOsmol/L.

In certain embodiments, an abuse-deterrent oral solid dosage form comprises a controlled release matrix comprising an active agent susceptible to abuse, a tonicity-increasing agent and a hydrophobic material, wherein the active agent and the tonicity-increasing agent are interspersed in the controlled release matrix and are released from the dosage form at the same or substantially the same rate (i.e., the rates that do not vary by more than 15%, the tonicity-increasing agent is in an effective amount to provide a hypertonic solution, suspension or gel of the active agent upon contact of the dosage form with 10 ml, or with from about 2 ml to about 5 ml, of a solvent, and the dosage form releases the active agent and the tonicity-increasing agent at a controlled release rate for about 6, about 8, about 10, about 12, about 16, about 18, about 20, about 24, about 28 or about 30 hours after placement of the dosage form in 900 ml of water. In certain embodiments, the dosage form releases about 0.8 mg, about 1.25 mg, about 1.7 mg, about 2.5 mg, about 3.3 mg, about 4.2 mg, about 5 mg, about 5.8 mg, about 6.7 mg, about 7.5 mg, about 8.3 mg, about 9.2 mg, about 10 mg, about 10.8 mg, about 11.7 mg, about 12.5 mg, or about 13.3 mg per hour of the active agent.

In additional embodiments, the tonicity-increasing agent and the active agent are released from the dosage form at different rates. For example, a tampered dosage form (e.g., a crushed dosage form) may release the tonicity-increasing agent at a faster rate than the rate of release of the active agent.

In certain embodiments, an abuse-deterrent oral solid dosage form comprises a plurality of particles, each particle comprising a core comprising an antagonist of an active agent susceptible to abuse, the core coated with a layer comprising the active agent susceptible to abuse and a tonicity-increasing agent, wherein the tonicity-increasing agent is in an effective amount to provide a hypertonic solution, suspension or gel of the active agent upon contact of the dosage form with 10 ml, or with from about 2 ml to about 5 ml, of a solvent.

In certain embodiments, an abuse-deterrent oral dosage form comprises a plurality of particles, each particle comprising a core comprising an antagonist of an active agent susceptible to abuse, the core coated with a layer comprising (i) oxycodone, hydrocodone, hydromorphone, morphine, oxymorphone, or a pharmaceutically acceptable salt of any of the foregoing, and (ii) a tonicity-increasing agent, wherein the tonicity-increasing agent is in an effective amount to provide a hypertonic solution, suspension or gel of an osmolality sufficient to deter abuse of said oxycodone, hydrocodone, hydromorphone, morphine, oxymorphone, or pharmaceutically acceptable salt of any of the foregoing upon contact of the dosage form with 10 ml, or with from about 2 ml to about 5 ml, of a solvent (e.g., distilled water). In certain embodiments, the antagonist of the active agent susceptible to abuse is naltrexone or a pharmaceutically acceptable salt thereof.

In further embodiments, an abuse-deterrent dosage form comprises a plurality of particles, each particle comprising a core comprising an antagonist of an active agent susceptible to abuse, the core coated with a first layer comprising the active agent susceptible to abuse and a second layer surrounding the first layer comprising a tonicity-increasing agent, wherein the tonicity-increasing agent is in an effective amount to provide a hypertonic solution or suspension of an osmolality sufficient to deter abuse of the active agent upon contact of the dosage form with 10 ml, or with from about 2 ml to about 5 ml, of a solvent. In certain embodiments, the active agent susceptible to abuse is an opioid agonist (e.g., oxycodone, hydrocodone, hydromorphone, morphine, oxymorphone, or a pharmaceutically acceptable salt of any of the foregoing); and the antagonist is naltrexone or a pharmaceutically acceptable salt thereof.

In additional embodiments, an abuse-deterrent dosage form comprises a plurality of particles, each particle comprising a core comprising an antagonist of an active agent susceptible to abuse, the core coated with a first layer comprising the active agent susceptible to abuse and a second layer surrounding the first layer comprising a tonicity-increasing agent, wherein the tonicity-increasing agent is in an effective amount to provide a hypertonic solution or suspension of an osmolality sufficient to deter abuse of the active agent upon contact of the dosage form with 10 ml, or with from about 2 ml to about 5 ml, of a solvent, wherein the antagonist is sequestered in each particle.

In additional embodiments, an abuse-deterrent dosage form comprises a plurality of particles, each particle comprising a core comprising an antagonist of an active agent susceptible to abuse, the core coated with a first layer comprising the active agent susceptible to abuse and a second layer surrounding the first layer comprising a tonicity-increasing agent, wherein the tonicity-increasing agent is in an effective amount to provide a hypertonic solution or suspension of an osmolality sufficient to deter abuse of the active agent upon contact of the dosage form with 10 ml, or with from about 2 ml to about 5 ml, of a solvent, wherein the antagonist is sequestered such that an amount of the opioid antagonist released from the dosage form which has been orally administered intact is less than the amount bioequivalent to 0.125 mg of naltrexone, based on the in-vitro dissolution at 1 hour of the dosage form in 900 ml of Simulated Gastric Fluid using a USP Type II (paddle) apparatus at 75 rpm at 37° C., and is insufficient to produce a physiological effect of the opioid antagonist in a mammal, and the amount of the opioid antagonist released from the dosage form which has been subjected to tampering is an amount bioequivalent to 0.25 mg of naltrexone or more, based on the in-vitro dissolution at 1 hour of the dosage form in 900 ml of Simulated Gastric Fluid, as determined by 37 USP Type II dissolution apparatus (paddle) at 75 rpm at 37° C., and will produce a physiological effect of the opioid antagonist in a mammal.

In other embodiments, an abuse-deterrent dosage form is a transdermal dosage form comprising an active agent susceptible to abuse and a tonicity-increasing agent, wherein the tonicity-increasing agent is in an effective amount to provide a hypertonic solution or suspension of the active agent upon contact of the dosage form with a solvent comprising 10 ml of distilled water.

In certain embodiments, an abuse-deterrent dosage form is a transdermal dosage form comprising an active agent susceptible to abuse and a tonicity-increasing agent, wherein the tonicity-increasing agent is in an effective amount to cause pain or discomfort in a mammal upon contact of a portion of the transdermal dosage form with an oral mucosal membrane of the mammal. In certain embodiments, the active agent susceptible to abuse is an opioid agonist.

In certain embodiments, an abuse-deterrent transdermal delivery system comprises (i) an active agent susceptible to abuse, (ii) a polymer, (iii) a softening agent; and (iv) a tonicity-increasing agent, wherein the tonicity-increasing agent is not released from the transdermal delivery system attached to the skin of a mammal, but is released from the transdermal delivery system in an amount to cause pain or burning when attached to an oral mucosal membrane of the mammal.

In additional embodiments, an abuse-deterrent transdermal dosage form comprises an active agent susceptible to abuse and a tonicity-increasing agent, wherein the tonicity-increasing agent is in an effective amount to provide a hypertonic solution, suspension or gel of the active agent within about 1 second to about 10 minutes after contact of the dosage form with a mucosal membrane of a mammal (e.g. human). In some of these embodiments, the tonicity-increasing agent is in an effective amount to provide a hypertonic solution, suspension or gel of the active agent within 3 seconds, 5 seconds, 10 seconds, 15 seconds, 30 seconds, 45 seconds, 1 minute, 2 minutes, 3 minutes, 5 minutes, 6 minutes, 7 minutes, 8 minutes or 10 minutes after contact of the dosage form with the mucosal membrane of the mammal.

In additional embodiments, an abuse-deterrent transdermal dosage form comprises an opioid agonist and a tonicity-increasing agent, wherein the tonicity-increasing agent is in an effective amount to provide a hypertonic solution, suspension or gel of the opioid agonist within 3 seconds, 5 seconds, 10 seconds, 15 seconds, 30 seconds, 45 seconds, 1 minute, 2 minutes, 3 minutes, 5 minutes, 6 minutes, 7 minutes, 8 minutes or 10 minutes after contact of the dosage form with the mucosal membrane of a mammal.

In further embodiments, an abuse-deterrent dosage form comprises an active agent susceptible to abuse and a tonicity-increasing agent, wherein the tonicity-increasing agent is in an effective amount to provide a hypertonic solution or suspension of the active agent upon contact of the tampered dosage form with 10 ml of a solvent, or with a nasal or oral mucosal membrane of a mammal.

The present invention also encompasses hypertonic solutions, suspensions and gels prepared by dissolving a crushed solid oral dosage forms in from about 2 to about 10 ml, preferably from about 2 ml to about 5 ml, of water, the solutions suspensions and gels having an osmolality sufficient to deter abuse of the solid dosage form (e.g., by an intravenous injection of the dissolved dosage form or snorting of the crushed dosage form). The osmolality of the solution, suspension or gel may generally be from about 300 mOsmol/L to about 10000 mOsmol/L, 380 mOsmol/L to about 10000 mOsmol/L, from about 380 mOsmol/L to about 5000 mOsmol/L, from about 380 mOsmol/L to about 2500 mOsmol/L, from about 380 mOsmol/L to about 880 mOsmol/L, or from about 1000 mOsmol/L to about 2500 mOsmol/L. In the preferred embodiments, the solid oral dosage form is crushed and dissolved in from about 2 ml to about 5 ml of water, and the resulting solution, suspension or gel has an osmolality of from about 1000 mOsmol/L to about 2500 mOsmol/L. These solutions, suspensions and gels may be used, e.g., as testing solution, suspensions or gels to determine if the solid oral dosage form is abuse-deterrent.

The present invention is also directed to methods of deterring abuse of pharmaceutical dosage forms, the methods comprising including a tonicity-increasing agent in the dosage form in an amount which will produce a hypertonic solution, suspension or a gel which is sufficiently hypertonic to deter abuse of the dosage form upon exposure of the dosage form to from about 1 ml to about 120 ml, from about 1 ml to about 100 ml, from about 1 ml to about 60 ml, or from about 1 ml to about 30 ml, from about 1 ml to about 10 ml, or from about 2 ml to about 5 ml of distilled water. In some of these methods, two or more tonicity-increasing agents are included in the dosage form.

The present invention is also directed to methods of deterring abuse of pharmaceutical dosage forms (e.g., oral solid dosage forms), the methods comprising including a tonicity-increasing agent in the dosage form in an amount which will produce a hypertonic solution, suspension or gel having an osmolality of from about 300 to about 3,000 mOsmol/L, from about 300 to about 880 mOsmol/L (sodium chloride equivalency of the solution is between about 0.9% to 3% sodium chloride), from about 880 mOsmol/L to about 2500 mOsmol/L, or from about 1000 mOsmol/L to about 2500 mOsmol/L upon exposure of the dosage form to from about 1 ml to about 120 ml, from about 1 ml to about 100 ml, from about 1 ml to about 60 ml, from about 1 ml to about 30 ml of water, from about 1 ml to 10 ml, or from about 2 ml to about 5 ml of distilled water. In certain embodiments, the osmolality of the solution, suspension or gel is from about 300 mOsmol/L to about 380 mOsmol/L, from about 300 mOsmol/L to about 320 mOsmol/L from about 880 mOsmol/L to about 2500 mOsmol/L, or from about 1000 mOsmol/L to about 2500 mOsmol/L, upon exposure of the dosage form to 10 ml or from about 2 ml to 5 ml of water. In the preferred embodiments, the osmolality of the solution, suspension or gel is sufficient to cause pain or burning at the site of administration when the dosage form is dissolved in from 1 to 10 ml of water and administered by injection (e.g., intravenous injection) or is crushed and applied to a mucosal membrane (e.g., oral or nasal). The pain and burning is preferably sufficient to deter abuse of the dosage forms by intravenous injection, snorting or buccal administration.

The present invention is also directed to methods of lowering an abuse potential of deterring abuse of a pharmaceutical dosage form, the methods comprising including a tonicity-increasing agent in the dosage form in an amount which will produce a hypertonic solution, suspension or a gel which is sufficiently hypertonic to deter abuse of the dosage form upon exposure of the dosage form to from about 1 ml to about 120 ml, from about 1 ml to about 100 ml, from about 1 ml to about 60 ml, or from about 1 ml to about 30 ml, from about 1 ml to about 10 ml, or from about 2 ml to about 5 ml of distilled water. In some of these methods, two or more tonicity-increasing agents are included in the dosage form.

The present invention is further directed to methods of using abuse-deterrent pharmaceutical dosage forms of the invention to treat medical conditions (e.g., pain, anxiety, insomnia, depression, epilepsy, narcolepsy, etc.) comprising administering an abuse-deterrent dosage form according to the present invention to a mammal at a dose and via a route recommended by the manufacturer of the pharmaceutical dosage form.

DEFINITIONS

The term "about" in the present specification means a value within 15% (±15%) of the value recited immediately after the term "about," including the value equal to the upper limit (i.e., +15%) and the value equal to the lower limit (i.e., −15%) of this range. For example, the phrase "about 100" encompasses any numeric value that is between 85 and 115, including 85 and 115.

The phrase "a controlled release of the active agent" in the present specification means that the active agent is released for at least 6 hours to 24 hours and such that not more than 30% of the active agent is released from an intact dosage form within 1 hour of placing the dosage form in 900 ml of water, as determined by USP 37 Type II dissolution apparatus (Paddle), 75 rpm at 37° C.

The phrase "deter abuse" as used in the present specifications means to lower an abuse potential of a dosage form, as compared to an identical dosage form but without the tonicity-increasing agent.

The phrase "an immediate release of the active agent" in the present specification means that at least 75% of the active agent is released from an intact dosage form within 1 hour of placing the dosage form in 900 ml of water, as determined by USP 37 Type II dissolution apparatus (Paddle), 75 rpm at 37° C.

The term "hypertonic" as used in the present specification means hypertonic to 0.9% sodium chloride distilled water solution.

The term "solvent" in the present specification includes solvents of a type used by addicts attempting to abuse dosage forms. The term includes, e.g., water, alcohols, ketones, and mixtures comprising one or more of the foregoing. The term also includes saliva and nasal secretions.

The term "water" as used in the present specification includes distilled water.

DETAILED DESCRIPTION

A solution is isotonic to a mammal's physiological fluid if it has the same osmolality or osmotic pressure as the mammal's physiological fluid (typically about 280 to 290 mOsmol/L). Solutions with an osmotic pressure lower than that of physiological fluids are considered hypotonic. Solutions having a greater osmotic pressure than that of physiological fluids are considered hypertonic.

A serum osmolality outside the 280 to 290 mOsmol/L range is often accompanied by one or more symptoms. For example, a serum osmolality level of between about 294 mOsmol/L and about 298 mOsmol/L is associated with thirst in an alert and communicative subject or patient. A serum osmolality level of from about 299 mOsmol/L to about 313 mOsmol/L is associated with dry mucous membranes. A serum osmolality level of from about 314 mOsmol/L to about 329 mOsmol/L is associated with weakness and doughy skin. A serum osmolality level of above 330 mOsmol/L is associated with disorientation, postural hypotension, severe weakness, fainting, CNS changes and coma.

However, when a small amount of a hypertonic solution, suspension or gel (e.g., from about 0.5 ml to about 30 ml of a 0.95% to 3% or a 1 to 7% solution of sodium chloride) is introduced into the systemic circulation of a subject, the subject will experience pain and burning at the injection site only. This is partly because, upon introduction, the hypertonic solution, suspension or gel will then be diluted by the circulating blood. In an adult human, the volume of the circulating blood is from about 4 to about 6 liters. Thus, the introduction of the small amount of the hypertonic solution, suspension or gel into the systemic circulation should not cause any systemic effects (e.g., cardiovascular or CNS effects) in the subject.

In addition, the body has mechanisms for maintaining the osmolality of the bodily fluids (blood, lacrimal fluid, gastrointestinal tract) at a constant level. The body normally adjusts so as to keep the osmolality of the bodily fluids at from about 280 to 290 mOsmol/L, e.g., by controlling the release of antidiuretic hormone (ADH) from the pituitary gland or by controlling urinary flow and the feeling of thirst. For example, an increase of plasma osmoticity of 1% will typically stimulate the release of ADH, result in a reduction of urine flow, and stimulate thirst. See, e.g., Remington, The Science and Practice of Pharmacy, page 251 (2005). The reduction of urinary output and an increase in water intake will tend to lower the osmolality back to the normal level (280 to 290 mOsmol/L).

Traditionally, in an effort to minimize pain and discomfort at the administration site, pharmaceutical dosage forms intended for administration intravenously or via mucosal membranes were formulated to be isotonic with a mammal's physiological fluid at the site of intended administration (e.g., blood or lacrimal fluid).

In the present invention, pharmaceutical dosage forms are formulated so that a hypertonic solution, suspension or gel results from exposure of the dosage form to a small amount of a solvent (e.g., from about 0.5 ml to about 120 ml, from about 0.5 ml to about 30 ml or about 10 ml, or from about 2 ml to about 5 ml of distilled water).

If injected intravenously, this hypertonic solution, suspension or gel is intended in some embodiments (e.g., when the dosage form is administered contrary to the route recommended by the manufacturer of the dosage form) to cause discomfort (e.g., pain or burning) at the injection site.

If contacted with oral or nasal mucosal membranes, this hypertonic solution, suspension or gel is intended in some embodiments (e.g., when the dosage form is administered contrary to the route recommended by the manufacturer of the dosage form) to cause discomfort (e.g., pain or burning) at the contact site.

Generally, pain resulting from inappropriate use of a dosage form according to the present invention occurs instantaneously or within 10 seconds of the injection or the contact with the oral and nasal membrane. The pain may be characterized as "sharp," "dull," "severe aching," "throbbing," "stinging," and/or "burning." The pain generally lasts from about 5 minutes to about 14 days, from about 10 minutes to about 12 days, from about 20 minutes to about 10 days, from about 30 minutes to about 7 days, from about 1 hour to about 7 days, from about 1.5 hours to about 7 days, from about 2 hours to about 7 days, from about 2.5 hours to about 7 days, from about 3 hours to about 6 days, from about 3 hours to about 5 days, from about 4 hours to about 4 days, from about 5 hours to about 3 days, from about 5 hours to about 2 days, from about 5 hours to about 40 hours, from about 6 hours to about 36 hours, or from about 6 hours to about 24 hours. In certain embodiments, the pain lasts from about 3 hours to about 12 or 24 hours. In the preferred embodiments, the pain lasts for at least 30 minutes.

In certain embodiments, the pain may be accompanied by one or more of the following symptoms: radiating soreness or shooting pain at a distance, parestheisas, hyperesthesia of overlying areas or at a distant location, isolated local muscle spasms, muscle stiffness, increased or decreased cutaneous temperature.

If taken orally in an amount which exceeds the amount recommended by the manufacturer of the dosage form, the resulting hypertonic solution, suspension or gel is intended in some embodiments to cause GI irritation, diarrhea and/or increased urination.

Discomfort produced by injection or application of the transdermal dosage form or the tampered oral solid dosage form to the oral or nasal mucosal membrane is useful to deter abuse of the dosage form.

Dosage Forms

A dosage form in accordance with the present invention comprises an active agent susceptible to abuse, a tonicity-increasing agent(s) and one or more pharmaceutically acceptable excipients. Each component of the dosage form has a potential to contribute to the osmotic pressure of the solution, suspension or gel formed when the dosage form is dissolved in a solvent. In certain embodiments, the dosage form comprises one or more additional abuse-deterrent agents (e.g., gelling agents, irritants, bittering agents, surfactants, staining agents, laxatives, pharmacological antagonists of the active agent, etc.).

The active agent susceptible to abuse generally comprises from about 1% to about 99% of the dosage form by weight.

The tonicity-increasing agent(s) generally comprises from about 0.01% to about 90% or from about 0.01% to about 45% of the dosage form by weight.

The one or more pharmaceutically acceptable excipients generally comprise from about 1% to about 99% of the composition by weight.

The one or more additional abuse-deterrent agents generally comprise from about 0.1% to about 95% of the dosage form by weight.

A dosage form of the invention may be an oral dosage form (e.g., a mini-tablet, a tablet, a capsule, etc.), or a transdermal delivery system (e.g., a transdermal patch, transdermal gel, etc.), or a vaginal or rectal suppository.

The tonicity-increasing agent may be released from the dosage form before, during and/or after the active agent is released from the dosage form.

The tonicity-increasing agent and the active agent may be released from the dosage form at the same or at different times.

The tonicity-increasing agent and the active agent may be released from the dosage form at the same or different rates.

Active Agents Susceptible to Abuse

Active agents susceptible to abuse include, e.g., opioid analgesics, benzodiazepines, barbiturates, stimulants, and other drugs that may cause psychological and/or physical dependence.

Opioid Analgesics

In certain embodiments, an active agent susceptible to abuse is an opioid analgesic.

An opioid analgesic may be selected from the group comprising alfentanil, buprenorphine, butorphanol, carfentanil, codeine, dipanone, fentanyl, hydrocodone, hydromorphone, oxycodone, oxymorphone, levorphanol, lofentanil, morphine, meperidine, methadone, remifantil, heroin, tramadol, etorphine, dihydroetorphine, sufentanil, and the stereoisomers, polymorphs, metabolites, prodrugs, pharmaceutically acceptable salts, and mixtures thereof.

In certain embodiments, the opioid analgesic is selected from the group consisting of morphine, hydromorphone, hydrocodone, oxycodone, codeine, levorphanol, meperidine, methadone, oxymorphone, buprenorphine, fentanyl, dipipanone, heroin, tramadol, etorphine, dihydroetorphine, butorphanol, levorphanol, and the stereoisomers, polymorphs, active metabolites, prodrugs, pharmaceutically acceptable salts, and mixtures thereof.

In certain embodiments, the opioid analgesic is selected from the group consisting of hydrocodone, hydromorphone, oxycodone, morphine, and the stereoisomers, polymorphs, salts, active metabolites, prodrugs, pharmaceutically acceptable salts, and mixtures thereof.

In embodiments where the active agent susceptible to abuse is hydrocodone or a pharmaceutically acceptable salt thereof, the dosage form may comprise from about 5 mg to about 360 mg of the active agent. In certain embodiments, the dosage form comprises about 5 mg, about 7.5 mg, about 10 mg, about 12.5 mg, about 15 mg, about 17.5 mg, about 20 mg, about 25 mg, about 30 mg, about 40 mg, about 50 mg, about 60 mg, about 70 mg, about 80 mg, about 90 mg, about 100 mg, about 110 mg, about 120 mg, about 140 mg, about 150 mg, about 160 mg, about 170 mg, about 180 mg, about 190 mg, about 200 mg, about 210 mg, about 220 mg, about 230 mg, about 240 mg, or about 260 mg of the active agent. In some of these embodiments, the dosage form comprises 20 mg, 40 mg, 60 mg, 80 mg, 100 mg or 120 mg of hydrocodone or an equivalent amount of a pharmaceutically acceptable salt thereof (e.g., hydrocodone bitartrate).

In embodiments where the active agent susceptible to abuse is oxycodone or a pharmaceutically acceptable salt thereof, the dosage form may comprise from about 5 to about 360 mg of the active agent. In certain embodiments, the dosage form comprises about 5 mg, about 10 mg, about 15 mg, about 20 mg, about 30 mg, about 40 mg, about 60 mg, about 80 mg, about 100 mg, about 120 mg, about 140 mg, about 160 mg, or about 180 mg of the active agent. In some of these embodiments, the dosage form is a mini-tablet and comprises about 5 mg of oxycodone or a pharmaceutically acceptable salt thereof (e.g., oxycodone hydrochloride).

In embodiments where the active agent susceptible to abuse is hydromorphone or a pharmaceutically acceptable salt thereof, the dosage form comprises from about 2 to about 50 mg of the active agent. In certain embodiments, the dosage form comprises about 2 mg, about 4 mg, about 6 mg, about 8 mg, about 10 mg, about 12 mg, about 16 mg, about 20 mg, about 36 mg, about 32 mg or about 40 mg of the active agent.

In embodiments, where the active agent susceptible to abuse is morphine or a pharmaceutically acceptable salt thereof, the dosage form comprises from about 15 to about 600 mg of the active agent. In certain embodiments, the dosage form comprises about 15 mg, about 30 mg, about 45 mg, about 60 mg, about 80 mg, about 100 mg, about 120 mg, about 160 mg, or about 200 mg of the active agent.

Benzodiazepines

In certain embodiments, an active agent susceptible to abuse is a benzodiazepine. A "benzodiazepine" for the purposes of the present application means a compound which binds to a benzodiazepine receptor.

A benzodiazepine may be selected from the group consisting of alprazolam, bretazenil, bromazepam, brotizolam, chlordiazepoxide, cinolazepam, clonazepam, cloxazolam, clrorazepate, delorazepam, diazepam, estazolam, etizolam, flunitrazepam, flurazepam, flutoprazepam, halazepam, ketazolam, loprazolam, lorazepam, lormetazepam, medazepam, midaxolam, mimetazepam, nitrazepam, nordazepam, oxazepam, phenazepam, pinazepam, prazepam, premazepam, quazepam, temazepam, tetrazepam, triazolam, clobazam, escopiclone, zalepton, zolpidem, zopiclone, stereoisomers, polymorphs and pharmaceutically acceptable salts thereof.

In certain embodiments, the benzodiazepine is alprazolam, clonazepam, diazepam, estazolam, flumazepam, lorazepam, oxazepam, temazepam, stereoisomers, polymorphs or a pharmaceutically acceptable salt thereof.

The dosage form may comprise from about 0.25 mg to about 100 mg of the benzodiazepine. In embodiments where the dosage form is an oral solid dosage form, the dosage form may comprise about 0.25 mg, 0.5 mg, 1 mg, 2 mg, 5 mg, 10 mg, 15 mg, 20 mg, 30 mg, 60 mg, or 90 mg of the benzodiazepine.

Barbiturates

In certain embodiments, an active agent susceptible to abuse is a barbiturate. A barbiturate may be selected from the group consisting of amobarbital, allobarbital, aphenal, amobarbital, aprobarbital, benzobarbital, butalbital, phenobarbital, pentobarbital, secobarbital, polymorphs thereof, and pharmaceutically acceptable salts thereof.

In certain embodiments, the barbiturate is amobarbital, pentobarbital, secobarbital, phenobarbital, or a pharmaceutically acceptable salt thereof.

The dosage form may comprise from about 1 mg to about 100 mg of the barbiturate. In embodiments where the dosage form is an oral solid dosage form, the dosage form may comprise about 1 mg, 5 mg, 10 mg, 15 mg, 20 mg, 30 mg, 40 mg, 50 mg, 60 mg, 60 mg, or 90 mg of the barbiturate.

Stimulants

In certain embodiments, an active agent susceptible to abuse is a stimulant. A stimulant may be selected from the group consisting of amphetamines, methamphetamines, amphetamine and methamphetamine precursors (e.g., ephedrine, pseudoephedrine, phenylpropanolamine, etc.), norpseudoephedrine, methylphenidate, caffeine, nicotine, norephinephrine reuptake inhibitors, norepinephrine-dopamine reuptake inhibitors, modafinil, adrafinil, armodafinil, ampakines, derivatives, polymorphs, pharmaceutically acceptable salts, and mixtures thereof.

In certain embodiments, the stimulant is methylphenidate or a pharmaceutically acceptable salt thereof.

The dosage form may comprise from about 10 mg to about 200 mg of the stimulant. In embodiments where the dosage form is an oral solid dosage form, the dosage form may comprise about 10 mg, 15 mg, 20 mg, 30 mg, 40 mg, 50 mg, 60 mg, 70 mg, 80 mg, 90 mg, or 100 mg of the stimulant.

Tonicity-Increasing Agents

A dosage form in accordance with the present invention includes one or more tonicity-increasing agents. Tonicity-increasing agents are osmotically active compounds.

For the purposes of the present application, "tonicity-increasing agents" do not include "irritants" described below.

Tonicity-increasing agents include, e.g., osmotically active salts, acids, bases, chelating agents, and other organic and inorganic compounds or solutes. In certain embodiments, osmotically active compounds include calcium bicarbonate, calcium sulfate, calcium lactate, magnesium sulfate, magnesium chloride, sodium chloride, sodium sulfite, lithium chloride, lithium sulfate, potassium sulfate, potassium chloride, mannitol, urea, tartaric acid, raffinose, alpha-d-lactose monohydrate, sucrose, glucose, osmotically active compounds described in U.S. Pat. Nos. 3,854,770; 4,077,407; and 4,235,236, herein incorporated by reference, and the like. In certain embodiments, the tonicity increasing agent is selected from the group consisting of glycerin, lactose, mannitol, dextrose, sodium salts (e.g., sodium chloride, sodium sulfate, etc.), potassium salts (e.g., potassium phosphate dibasic, etc.), magnesium salts, sorbitol and the like. In certain embodiments, tonicity-increasing agents include mannitol, sorbitol, lactose, sodium salts and combinations thereof. In certain embodiments, the tonicity-increasing agent is a sodium salt (e.g. sodium chloride or sodium bicarbonate) or a potassium salt (e.g., potassium phosphate dibasic). In certain embodiments, the tonicity increasing agent comprises dextrose and either a sodium salt or a potassium salt. In additional embodiments, the tonicity-increasing agent comprises a mixture of (i) dextrose and (ii) an agent selected from the group consisting of glycerin, lactose, mannitol, dextrose, sodium salts, calcium salts, potassium salts, magnesium salts, and sorbitol. In some of these embodiments, the tonicity-increasing agent comprises a mixture of dextrose and sodium chloride.

In certain preferred embodiments, the tonicity-increasing agent is an osmatically active compound selected from the group consisting of carbohydrates (e.g., dextrose, lactose, etc.), salts, mannitol, urea, acids (e.g., tartaric acid), and combinations of any of the foregoing. In some of these embodiments, the tonicity-increasing agent is a carbohydrate or a pharmaceutically acceptable salt thereof. In additional embodiments, the tonicity increasing agent is a pharmaceutically acceptable salt of sodium, potassium, calcium or magnesium.

Although these compounds may have been used in pharmaceutical dosage forms prior to the present invention, it is believed that these compounds were not used as tonicity-increasing agents and in the amounts contemplated by the present invention. For example, it is believed that prior to the present invention, osmotic dosage forms contained osmotically active compounds but did not release these compounds upon placement of the dosage forms into 10 ml of distilled water and did not intend for the osmotically active compounds to be used as abuse-deterrent agents. These compounds remained in the osmotic dosage forms, while the active agents were released. These compounds were in contact with the solvent entering the dosage form and therefore were not "sequestered" as described herein below. It is further believed that, prior to the present invention, dosage forms comprising active agents susceptible to abuse (e.g., opioid agonists) did not form hypertonic solutions, suspensions or gels of a sufficient osmolality to deter abuse of the dosage forms upon dissolution of these dosage forms in 10 ml or in from 2 ml to 5 ml of distilled water as described in the present specification, because these dosage forms were widely abused by parenteral routes. Had these dosage forms formed hypertonic solutions, suspensions or gels of a sufficient osmolality upon dissolution of these dosage forms in 10 ml or in from 2 ml to 5 ml of distilled water as described in the present specification, it is believed that these dosage forms would not have been abused by parenteral routes so widely.

An amount of the tonicity-increasing agent(s) in the dosage form of the present invention will vary between dosage forms having different compositions. Generally, the amount of the tonicity-increasing agent(s) in the dosage form is such that the dosage form, upon exposure to from about 1 to about 120 ml, and particularly about 10 ml or from about 2 ml to about 5 ml, of a solvent (e.g., distilled water) produces a solution, suspension or gel with an osmolality equivalent to or higher than the osmolality of a solution comprising from about 0.95% to about 20% of sodium chloride by weight, and preferably with an osmolality sufficient to deter abuse of the dosage forms. In certain embodiments, the osmolality of the resulting solution, suspension or gel is equivalent to or higher than the osmolality of a solution comprising from about 0.95% to about 15%, from about 1% to about 10%, from about 1% to about 9%, from about 1% to about 8%, from about 1% to about 6%, from about 1% to about 5%, from about 0.95% to about 3%, or from about 3% to about 7% sodium chloride by weight. In the preferred embodiments, the osmolality of the resulting solution, suspension or gel is higher than the osmolality of the 0.9% sodium chloride distilled water solution, is sufficient to deter abuse and is insufficient to raise the serum osmolality of a subject abusing the dosage form above 314 mOsmol/l or 330 mOsmol/L.

In certain embodiments directed to solid, oral dosage form, the tonicity-increasing agent (e.g., dextrose) is used as a filler of the dosage form.

The amount of a tonicity-increasing agent to be included in the dosage form may be determined, e.g., by (i) dissolving an existing dosage form in 10 ml of distilled water, (ii) measuring the osmolality of the resulting solution, and (iii) calculating the amount of the tonicity-increasing agent (e.g., sodium chloride) that would be required to produce an osmolality sufficient to deter abuse (e.g., an osmolality of from 1200 mOsmol/10 ml to about 1256 mOsmol/10 mL or from about 380 mOsmol/L to about 10000 mOsmol/L, based on normal serum osmolality of 285 mOsmol/L, the maximum serum osmolality which should not be exceeded of 314 mOsmol/L, and the addict having 4 liters of blood), (iv) modifying or reformulating the existing formulation to include the required amount of sodium chloride or an equivalent amount of a different tonicity-increasing agent and, optionally, dissolving the reformulated formulation in 10 ml of distilled water and measuring the osmolality of the resulting solution to confirm that the resulting solution has the required osmolality.

The osmolality of the resulting solution may be measured by using an osmometer (e.g., Advanced® Osmometer Model 3250, manufactured by Advanced Instruments, Inc., the User's Guide (3255 Rev13 042710) of which is herein incorporated by reference).

In certain embodiments, where the E values for the components of the formulation are known, the amount of the tonicity-increasing agent to be included in the dosage forms of the invention may be calculated by the sodium chloride equivalency method. The E value is defined as the weight of sodium chloride that will produce the same osmotic effect as 1 gram of a particular compound. The E value for the particular compound in a particular formulation may be obtained from, e.g., Remington, The Science and Practice of Pharmacy, chapter 18, Appendix A (2005). The contribution of that compound to the osmolality of the solution, suspension or gel resulting from dissolution of the dosage form in 30 ml of distilled water is calculated by multiplying the E value of the compound by the concentration of the compound (in grams of the compound per 100 ml of the solution) and by 30 ml. The amount of sodium chloride which will be necessary to make the resulting solution isotonic is calculated by subtracting the calculated contribution of that compound to the osmolality of the solution from 0.270. An equivalent amount of a tonicity-increasing agent other than sodium chloride that would form an isotonic solution, suspension or gel when the dosage form is dissolved in 30 ml of distilled water may be calculated by dividing the calculated amount of sodium chloride necessary to make the resulting solution isotonic by the E value of the other tonicity-increasing agent. Amounts of the sodium chloride and the other tonicity-increasing agent that are higher than the calculated amounts which make the resulting solution isotonic will make the solution, suspension of gel resulting from dissolution of the dosage form in 30 ml of water hypertonic. Such higher amounts may therefore be included in the dosage form of the present invention, as long as these amounts are insufficient to raise the serum osmolality in an abuser above 314 mOsmol/L, based on simultaneous administration of up to five dosage units.

In certain embodiments, the tonicity-increasing agent is sodium bicarbonate, and the dosage form comprises from about 5% to about 90% or from about 7% to about 40% of sodium bicarbonate by weight. The dosage form may be a sustained release tablet, a sustained release mini-tablet or an immediate release tablet (e.g., an immediate release mini-tablet). In some of these embodiments, the dosage form comprises from about 15% to about 30% sodium bicarbonate by weight. In certain embodiments, the dosage form comprises about 20% sodium bicarbonate by weight.

In certain embodiments, the tonicity-increasing agent is potassium chloride and comprises about 5% to about 90% or from about 45% to about 30% of the dosage form by weight. In certain embodiments, the dosage form comprises about 10% potassium chloride by weight.

In certain embodiments, the tonicity-increasing agent is dextrose and comprises about 5% to about 90% of the dosage form by weight. In some of these embodiments, the formulation is free from microcrystalline cellulose.

In certain embodiments, a mixture of two or more of tonicity-increasing agents is used. For example, a mixture may comprise dextrose and either a sodium salt (e.g., sodium chloride) or a potassium salt (e.g., potassium phosphate dibasic). In some of these embodiments, dextrose may comprise from 40 to 90% of the formulation by weight and the sodium or potassium salt may comprise from about 5% to about 40% of the formulation by weight.

In certain embodiments, the amount of the tonicity-increasing agent is such that even if a subject administers 5 times the dose recommended by the manufacturer, the serum osmolality will not rise above 294 mOsmol/L, based on administration to the subject having an initial serum osmolality of from 280 to 290 mOsmol/L.

The tonicity-increasing agent comprises from about 0.01% to about 90%, from about 0.01% to about 45%, from about 0.05% to about 40%, from about 0.1% to about 40%, from about 0.1% to about 35%, from about 0.1% to about 30%, from about 0.3% to about 30%, from about 0.5% to about 25%, or from about 0.8% to about 25% of the dosage form by weight.

In certain embodiments, the tonicity-increasing agent comprises about 0.5%, 1%, 2%, 3%, 4%, 5%, 6%, 7%, 8%, 9%, 10%, 20%, 30%, 40%, 50% or 60% of the dosage form by weight.

In certain embodiments, the dosage form comprises from about 0.001 mg to about 2000 mg, from about 0.001 mg to about 800 mg, from about 0.02 mg to about 700 mg, from about 0.03 mg to about 600 mg, from about 0.04 mg to about 500 mg, from about 0.05 mg to about 400 mg, from about 0.06 mg to about 300 mg, from about 0.07 mg to about 200 mg, from about 0.08 mg to about 100 mg, from about 0.08 mg to about 50 mg, from about 0.09 mg to about 25 mg, or from about 0.1 mg to about 10 mg, or from about 0.8 mg to about 8 mg of the tonicity-increasing agent. In some of these embodiments, the tonicity-increasing agent is not sodium chloride. In some of these embodiments, the tonicity-increasing agent is dextrose, sodium bicarbonate or potassium chloride.

In certain embodiments, the tonicity-increasing agent is sodium chloride, and the dosage form comprises from about 0.01 mg to about 2000 mg, from about 0.01 mg to about 800 mg, from about 0.02 mg to about 700 mg, from about 0.03 mg to about 600 mg, from about 0.04 mg to about 500 mg, from about 0.05 mg to about 400 mg, from about 0.06 mg to about 300 mg, from about 0.07 mg to about 200 mg, from about 0.08 mg to about 100 mg, from about 0.08 mg to about 50 mg, from about 0.09 mg to about 25 mg, or from about 0.1 mg to about 10 mg, or from about 0.8 mg to about 8 mg of sodium chloride.

In certain embodiments, the dosage form comprises from about 0.001 mg to about 800 mg of the tonicity-increasing agent.

In certain embodiments, the tonicity-increasing agent is sodium chloride, and the dosage form comprising from about 0.1 mg to about 500 mg or from about 0.1 mg to about 100 mg of sodium chloride.

In certain embodiments, the tonicity-increasing agent is included in an amount which will provide an osmolality that is greater than the osmolality of from about 300 to about 880 mOsmol/L (sodium chloride equivalency of the solution is between about 0.9% to 3% sodium chloride), from about 880 mOsmol/L to about 2500 mOsmol/L or from about 1000 mOsmol/L to about 2500 mOsmol/L, when the dosage form is dissolved in from about 1 ml to about 120 ml of distilled water (e.g., 10 ml or from about 2 ml to about 5 ml of distilled water). In certain embodiments, the osmolality of the solution comprising a dissolved dosage form is from about 300 mOsmol/L to about 380 mOsmol/L, or from about 300 mOsmol/L to about 320 mOsmol/L.

In certain embodiments, the viscosity of the solution, suspension or gel obtained after crushing the dosage form and placing it in about 10 ml, from about 2 ml to about 5 ml, of water would be less than 8 cP. In some of these embodiments, the viscosity of the solution, suspension or gel would be form about 1 cP to about 7 cP.

The dosage form may comprise the tonicity-increasing agent in releasable form or in a sequestered form (i.e., the tonicity-increasing agent is combined with a sequestering material such that it is not released or substantially not released (i.e., less than 10% of the antagonist released from an intact dosage form at 24 hours after placing the dosage form in 900 ml of water, as determined by USP 37 Type II dissolution apparatus (Paddle), 75 rpm at 37° C.) unless the dosage form is tampered with (e.g., crushed to a powder)), or both in the releasable form and the sequestered form.

Releasable Forms of Tonicity-Increasing Agents

The tonicity-increasing agent may be included in the dosage form in a releasable form, meaning that at least 15% of the tonicity-increasing agent is released (separated) from an intact dosage form within from about 1 second to about 24 hours after placing the dosage form in 900 ml of water, as determined by USP 37 Type II dissolution apparatus (Paddle), 75 rpm at 37° C. The releasable form of the tonicity-increasing agent may provide for an immediate release of the tonicity-increasing agent (i.e., at least 75% of the active agent released or separated from the dosage form within 1 hour of placing the dosage form in 900 ml of water, as determined by USP 37 Type II dissolution apparatus (Paddle), 75 rpm at 37° C.) or a controlled release (i.e., release of a tonicity-increasing agent at a controlled rate over 6 hours to 24 hours for an oral dosage form or from about 8 hours to 240 hours for a transdermal dosage form, provided that not more than 30% of the active agent is released from the dosage form within 1 hour of placing the dosage form in 900 ml of water, as determined by USP 37 Type II dissolution apparatus (Paddle), 75 rpm at 37° C.).

In certain embodiments, a releasable form of the tonicity-increasing agent comprises a plurality of particles comprising the tonicity-increasing agent. In certain embodiments, the particles comprise the tonicity-increasing agent and one or more excipients. In certain embodiments, the particles comprise the tonicity-increasing agent, an active agent and one or more excipients. In certain embodiments, the particles comprise the tonicity-increasing agent, an active agent and a hydrophobic material comprising an acrylic polymer, a copolymer or acrylic acid and methacrylic acid, an alkylcellulose, a hydroxyalkylcellulose, or a mixture of two or more of the foregoing hydrophobic materials. In certain embodiments, the particles are free from the active agent.

In certain embodiments, a releasable form of the tonicity agent may comprise a core comprising the tonicity-increasing agent and one or more excipients. In certain embodiments, the core also includes the active agent. The core may provide an immediate release of the active agent (i.e., at least 75% of the active agent is released from the dosage form within 1 hour of placing the dosage form in 900 ml of water, as determined by USP 37 Type II dissolution apparatus (Paddle), 75 rpm at 37° C.) or a controlled release of the active agent for at least 6 hours to 24 hours and such that not more than 30% of the active agent is released from the dosage form within 1 hour of placing the dosage form in 900 ml of water, as determined by USP 37 Type II dissolution apparatus (Paddle), 75 rpm at 37° C.

In certain embodiments, a releasable form of the tonicity agent may comprise a core comprising a controlled release matrix comprising the tonicity-increasing agent and a hydrophobic material comprising an acrylic polymer, a copolymer or acrylic acid and methacrylic acid, an alkylcellulose, a hydroxyalkylcellulose, or a mixture of two or more of the foregoing materials. In certain embodiments, the core also includes the active agent.

In certain embodiments, a releasable form of the tonicity agent may comprise a core comprising an immediate release matrix comprising the tonicity-increasing agent and a hydrophobic or hydrophilic material comprising an acrylic polymer, a copolymer or acrylic acid and methacrylic acid, an alkylcellulose, a hydroxyalkylcellulose, or a mixture of two or more of the foregoing materials. In certain embodiments, the core also includes the active agent.

In certain embodiments, the releasable form of the tonicity-increasing agent comprises a layer of an oral, solid dosage form or a transdermal delivery system, the layer comprising the tonicity-increasing agent and one or more excipients. In the oral, solid dosage form, the layer may be a compressed layer or a sprayed/coated layer. In certain embodiments, the layer is coated over the oral, solid dosage form or over one or more particles contained in the dosage form. In certain embodiments, the layer is coated over a pharmaceutically acceptable core and under a layer comprising the active agent. In certain embodiments, the layer also includes the active agent.

In certain embodiments, the releasable form of the tonicity-increasing agent comprises a layer of an oral, solid dosage form or a transdermal delivery system, the layer comprising the tonicity-increasing agent and a hydrophobic material comprising an acrylic polymer, a copolymer or acrylic acid and methacrylic acid, an alkylcellulose, a hydroxyalkylcellulose, or a mixture of two or more of the foregoing materials. In the oral, solid dosage form, the layer may be a compressed layer or a sprayed/coated layer. In certain embodiments, the layer is coated over the oral, solid dosage form or over one or more particles contained in the dosage form. In certain embodiments, the layer is coated over a pharmaceutically acceptable core and under a layer comprising the active agent. In certain embodiments, the layer includes the active agent.

In certain embodiments, a releasable form of the tonicity-increasing agent may comprise a compressed blend of the tonicity-increasing agent and one or more excipients. In certain embodiments, the compressed blend also includes the active agent.

In certain embodiments, the releasable form of the tonicity-increasing agent comprises a core comprising the tonicity-increasing agent and an active agent, the core coated with a controlled release coating comprising one or more hydrophobic materials. In certain embodiments, the core comprises an active agent.

Sequestered Forms of Tonicity-Increasing Agent

In certain embodiments, the tonicity-increasing agent may be included in the dosage form in a sequestered form, meaning that the tonicity-increasing agent is not released to any substantial extent from the dosage form which is administered intact as intended by the manufacturer and was not in contact with the fluid entering the intact dosage form (i.e., less than 10% of the antagonist released from an intact dosage form at 24 hours after placing the dosage form in 900 ml of water, as determined by USP 37 Type II dissolution apparatus (Paddle), 75 rpm at 37° C.) unless the dosage form is tampered with (e.g., crushed to a powder)), but is released from the dosage form which has been tampered with (e.g., a dosage form which has been crushed and dissolved in from 2 to 5 ml of water). In these embodiments, tampering of the dosage form (e.g., by crushing) comprises the integrity of the sequestered tonicity-increasing agent structures (e.g., particles of the sequestered tonicity-increasing agent) and expose the tonicity increasing agent to a solvent, thereby providing a hypertonic solution, suspension or gel, having an osmolality which, in the preferred embodiments is sufficiently hypertonic to deter abuse.

A sequestered form of a tonicity-increasing agent may comprise a plurality of particles comprising a tonicity-increasing agent dispersed in a matrix comprising a pharmaceutically acceptable sequestering material (e.g., a hydrophobic polymer); or a tonicity-increasing agent coated with a layer comprising a pharmaceutically acceptable sequestering material (e.g., a hydrophobic polymer); or a tonicity-increasing agent dispersed in a matrix comprising a pharmaceutically acceptable sequestering material (e.g., a hydrophobic polymer), the matrix coated with a layer comprising an additional sequestering material (e.g., a hydrophobic polymer); or a tonicity-increasing agent coated with a layer comprising a pharmaceutically acceptable sequestering material (e.g., a hydrophobic polymer), the coated tonicity-increasing agent dispersed in a matrix comprising the additional sequestering material (e.g., a hydrophobic polymer). In certain embodiments, the sequestering material in the layer is the same as the sequestering material in the matrix. In other embodiments, the sequestering material in the layer is different from the sequestering material in the matrix. The sequestering material isolates the tonicity-increasing agent from a fluid entering an intact dosage form and preferably completely prevents the tonicity-increasing agent from contacting the fluid entering the intact dosage form.

In certain embodiments, the sequestering material in the matrix and the sequestering material in the layer is each independently selected from the group consisting of (i) an alkylcellulose; (ii) an acrylic polymer; or (iii) mixtures thereof. In some of these embodiments, the sequestering in the matrix and the sequestering material in the layer may each independently comprise an alkylcellulose (e.g., ethylcellulose) and a hydroxyalkylcellulose (e.g, hydroxypropylcellulose). In additional embodiments, the sequestering in the matrix and the sequestering material in the layer may each independently comprise a copolymer of an acrylic and methacrylic acid.

In certain embodiments, the sequestered form of the tonicity-increasing agent is free from (i.e., does not contain) the active agent susceptible to abuse.

In certain embodiments, the pharmaceutically acceptable sequestering material comprises a hydrophobic polymer comprising a cellulose polymer and/or an acrylic polymer. The cellulose polymer may be selected from the group consisting of ethylcellulose, cellulose acetate, cellulose propionate (lower, medium or higher molecular weight), cellulose acetate propionate, cellulose acetate butyrate, cellulose acetate phthalate and cellulose triacetate. An example of ethylcellulose is one that has an ethoxy content of 44 to 55%. Ethylcellulose may be used in the form of an alcoholic solution. In certain other embodiments, the sequestering material comprises polylactic acid, polyglycolic acid or a co-polymer of the polylactic and polyglycolic acid.

In certain embodiments, the sequestering material may comprise a hydrophobic cellulose polymer selected from the group consisting of cellulose ether, cellulose ester, cellulose ester ether, and cellulose. The cellulosic polymers have a degree of substitution, D.S., on the anhydroglucose unit, from greater than zero and up to 3 inclusive. By degree of substitution is meant the average number of hydroxyl groups present on the anhydroglucose unit comprising the cellulose polymer that are replaced by a substituting group. Representative materials include a polymer selected from the group consisting of cellulose acylate, cellulose diacylate, cellulose triacylate, cellulose acetate, cellulose diacetate, cellulose triacetate, mono, di, and tricellulose alkanylates, moni, di, and tricellulose aroylates, and mono, di, and tricellulose alkenylates. Exemplary polymers include cellulose acetate having a D.S. up to 1 and an acetyl content up to 21%; cellulose acetate having an acetyl content up to 32 to 39.8%; cellulose acetate having a D.S. of 1 to 2 and an acetyl content of 21 to 35%; and cellulose acetate having a D.S. of 2 to 3 and an acetyl content of 35 to 44.8%.

More specific cellulosic polymers include cellulose propionate having a D.S. of 1.8 and a propyl content of 39.2 to 45% and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7%; cellulose triacylate having a D.S. of 2.9 to 3 such as cellulose triacetate, cellulose trivalerate, cellulose trilaurate, cellulose tripatmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentanoate, and coesters of cellulose such as cellulose acetate butyrate, cellulose acetate octanoate butyrate and cellulose acetate propionate.

Additional cellulose polymers useful for preparing a tonicity-increasing agent in a sequestered form include acetaldehyde dimethyl cellulose acetate, cellulose acetate ethylcarbamate, cellulose acetate methylcarbamate, and cellulose acetate dimethylaminocellulose acetate.

Acrylic polymers useful for preparing a tonicity-increasing agent in a sequestered form include, but are not limited to, acrylic resins comprising copolymers synthesized from acrylic and methacrylic acid esters (e.g., the copolymer of acrylic acid lower alkyl ester and methacrylic acid lower alkyl ester) containing about 0.02 to 0.03 mole of a tri (lower alkyl) ammonium group per mole of the acrylic and methacrylic monomers used. An example of a suitable acrylic resin is a polymer manufactured by Evonik and sold under the Eudragit® RS trademark. Eudragit® RS30D is preferred. Eudragit® RS is a water insoluble copolymer of ethyl acrylate (EA), methyl methacrylate (MM) and trimethylammoniumethyl methacrylate chloride (TAM) in which the molar ratio of TAM to the remaining components (EA and MM) is 1:40. Acrylic resins such as Eudragit® RS may be used in the form of an aqueous suspension.

In certain embodiments of the invention, the acrylic polymer may be selected from the group consisting of acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers.

When the a tonicity-increasing agent in a sequestered form comprises particles comprising a tonicity-increasing agent coated with a coating that renders the tonicity-increasing agent non-releasable or substantially non-releasable from the intact dosage form, and when a cellulose polymer or an acrylic polymer is used for preparation of the coating composition, suitable plasticizers including, e.g., acetyl triethyl citrate and/or acetyl tributyl citrate, may also be admixed with the polymer. The coating may also contain additives such as coloring agents, talc and/or magnesium stearate, which are well known in the coating art.

The coating composition may be applied onto the tonicity-increasing agent particles by spraying it onto the particles using any suitable spray equipment known in the art. For example, a Wuster fluidized-bed system may be used in which an air jet, injected from underneath, fluidizes the coated material and effects drying while the insoluble polymer coating is sprayed on. The thickness of the coating will depend on the characteristics of the particular coating composition being used.

In certain embodiments, the pharmaceutically acceptable sequestering material useful for preparing a tonicity-increasing agent in a sequestered form may comprise a biodegradable polymer comprising a poly(lactic/glycolic acid) ("PLGA"), a polylactide, a polyglycolide, a polyanhydride, a polyorthoester, polycaprolactones, polyphosphazenes, polysaccharides, proteinaceous polymers, polyesthers, polydioxanone, polygluconate, polylactic-acid-polyethylene oxide copolymers, poly(hydroxybutyrate), polyphosphoesther or mixtures or blends of any of these.

In certain embodiments, a biodegradable polymer comprises a poly(lactic/glycolic acid), a copolymer of lactic and glycolic acid, having molecular weight of about 2,000 to about 500,000 daltons. The ratio of lactic acid to glycolic acid is from about 100:0 to about 25:75, with the ratio of lactic acid to glycolic acid of 65:35 being preferred.

Poly(lactic/glycolic acid) may be prepared by the procedure set forth in U.S. Pat. No. 4,293,539 (Ludwig et al.), the disclosure of which is hereby incorporated by reference in its entirety. In brief, Ludwig prepares the copolymer by condensation of lactic acid and glycolic acid in the presence of a readily removable polymerization catalyst (e.g., a strong acid ion-exchange resin such as Dowex HCR-W2-H). The amount of catalyst is not critical to the polymerization, but typically is from about 0.01 to about 20 parts by weight relative to the total weight of combined lactic acid and glycolic acid. The polymerization reaction may be conducted without solvents at a temperature from about 100° C. to about 250° C. for about 48 to about 96 hours, preferably under a reduced pressure to facilitate removal of water and by-products. Poly(lactic/glycolic acid) is then recovered by filtering the molten reaction mixture in an organic solvent such as dichloromethane or acetone and then filtering to remove the catalyst.

Additional Abuse-Deterrent Agents

In addition to the tonicity-increasing agent(s), dosage forms of the present invention may include one or more additional abuse-deterrent agents.

Additional abuse-deterrent agents used in the dosage forms of the present invention include, e.g., gelling agents, irritants, bittering agents, surfactants, staining agents, laxatives, antagonists of active agents, emetics, etc.

Gelling Agents

In certain embodiments, the dosage form of the present invention comprises one or more gelling agent(s), in addition to the tonicity-increasing agent(s).

Gelling agents may comprise from about 3% to about 90% of the dosage form by weight.

A dosage form may comprise from about 2 mg to about 1500 mg of one or more gelling agents.

A gelling agent may further reduce/deter abuse of the dosage form by forming a viscous substance upon exposure of the crushed dosage form to from about 5 ml to about 30 ml, and preferably about 10 ml or from about 2 ml to about 5 ml of distilled water. In certain embodiments, the gelling agent is released when the dosage form is tampered with and provides a gel-like quality to the tampered dosage form (e.g., a dosage form crushed to a powder and dissolved in 10 ml of distilled water), which slows the release of the drug susceptible to abuse such that the abuser is less likely to obtain a rapid "high."

In certain embodiments, the gelling agent may reduce abuse by nasal inhalation (i.e., snorting) by forming a gel upon crushing which is unsuitable for intranasal administration (i.e., the active substance would be trapped in the gel and would not be available for absorption in the nasal cavity).

In certain embodiments, when the dosage form is crushed to a powder and exposed to about 10 ml or from about 2 ml to about 5 ml of water it will form a thick and viscous substance, which is unsuitable for injection (an abuser would have substantial difficulty injecting the dosage form, e.g., due to pain at the site of administration or difficulty pushing the substance through the syringe).

In certain embodiments, the resulting viscosity of the gel obtained from crushing the dosage form to a powder and dissolving it in about 10 ml or from about 2 ml to about 5 ml of distilled water is from about 10 cP to about 100,000 cP, from about 10 cP to about 80,000 cP, from about 10 cP to about 60,000 cP, from about 15 cP to about 60,000 cP, or from about 20 cP to about 50,000 cP. In certain embodiments, the viscosity of the viscous substance is at least about 60 cP.

In certain embodiments, the viscosity of the solution, suspension or gel obtained after crushing the dosage form to a powder and placing the crushed powder in about 10 ml of distilled water is 8 cP or less. In some of these embodiments, the viscosity of the solution or suspension is from about 1 cP to about 7 cP.

Suitable gelling agents include, e.g., compounds that, upon contact with a solvent (e.g., distilled water), absorb the solvent and swell, thereby forming a viscous or semi-viscous substance that significantly reduces and/or minimizes the amount of free solvent that can contain an amount of a solubilized drug or that can be drawn into a syringe. In certain embodiments, the viscous or gelled material can also reduce the overall amount of drug extractable with the solvent by entrapping the drug in a gel matrix.

In certain embodiments, the gelling agent is selected from sugars and sugar derived alcohols, starch and starch derivatives, cellulose derivatives (e.g., microcrystalline cellulose, sodium carboxymethyl cellulose, methylcellulose, ethyl cellulose, hydroxyethyl cellulose, hydroxypropyl cellulose, and hydroxypropyl methylcellulose), dextrins, alginates, gums (e.g., carrageenan, gum tragacanth, gum acacia, guar gum, locust bean gum), pectin, gelatin, kaolin, lecithin, polyvinylpyrrolidone, polyethylene glycol, polyethylene oxide, polyvinyl alcohol, surfactants (e.g., sodium lauryl sulfate), mixed surfactant/wetting agent systems, emulsifiers, other polymeric materials, and mixtures thereof.

In certain embodiments, a gelling agent may be selected from alginates, carrageenan, pectin, guar gum, modified starch, hydroxypropylmethylcellulose, methylcellulose, and other cellulosic materials such as sodium carboxymethylcellulose and hydroxypropyl cellulose.

In certain embodiments, a gelling agent may be selected from sugar alcohols, starches, microcrystalline cellulose, sodium carboxy methyl cellulose, methylcellulose, ethyl cellulose, gums, polyvinylpyrolidone, and mixtures of any of the foregoing. In certain embodiments, the gelling agent is selected from alginic acid, polyacrylic acid, karaya gum, traganth gum, polyethylene oxide, polyvinyl alcohol, and methyl cellulose (e.g., sodium carboxy methyl cellulose, hydroxyethyl methyl cellulose, hydroxypropyl methyl cellulose), and mixtures of any of the foregoing.

In certain embodiments, the gelling agent is polyethylene oxide. Polyethylene oxide may have an average molecular weight of from about 80,000 to about 10,000,000, or from about 100,000 to about 8,000,000, or from about 100,000 to about 7,000,000, or from about 300,00 to about 6,000,000, or from about 300,000 to about 5,500,000, or from about 500,000 to about 5,000,000 daltons.

In certain embodiments, the gelling agent is hydroxypropyl methylcellulose. In certain embodiments, the hydroxypropyl methyl cellulose has a molecular weight of from about 3,000 to about 2,000,000, or from about 5,000 to about 1,500,000, or from about 6,000 to about 1,500,000. In certain embodiments, hydroxypropyl cellulose has a molecular weight of from about 3,000 to about 6,000.

In certain embodiments, the gelling agent is a mixture of polyethylene oxide and hydroxypropyl methyl cellulose.

In certain embodiments, the gelling agent is a polyvinyl alcohol. A polyvinyl alcohol may have a molecular weight of from about 15,000 to about 300,000, or from about 20,000 to about 200,000, or from about 30,000 to about 180,000, or from about 40,000 to about 160,000.

In certain embodiments where the tonicity-increasing agent and the gelling agent are two different components, the tonicity-increasing agent is released from the dosage form before the gelling agent is released from the dosage form and/or before the gelling agent begins to swell upon placement of the dosage form in a solvent (e.g., distilled water). This action serves to deter abuse of a dosage form that releases a portion of active agent contained therein before the gelling agent can begin to swell.

In certain embodiments, it may take the gelling agent (e.g., polyethylene oxide) from 2 to 5 minutes to begin swelling, and some of the active agent susceptible to abuse may be released from the dosage form and extracted by an addict during this time. The tonicity-increasing agent released along with the active agent in this embodiment will produce a hypertonic liquid if, e.g., an addict attempts to dissolve the dosage form. If the addict then attempts to inject the extracted solution, the addict would experience burning or pain from injecting the hypertonic liquid formed by the dissolution of the dosage form.

In certain embodiments, the tonicity-increasing agent and the gelling agent are released from the dosage form at about the same time.

In certain embodiments, the gelling agent is the tonicity-increasing agent.

In certain embodiments, the gelling agent may be included in the dosage form in a sequestered form. The sequestered form of the gelling agent may be prepared as described above in the section describing preparation of the sequestered form of the tonicity-increasing agent.

Irritants

In certain embodiments, the dosage form of the present invention comprises one or more irritants.

An irritant is included in an effective amount to impart an irritating sensation to an abuser upon administration of said dosage form after tampering (e.g., snorting of the crushed dosage form, injection of a solution, suspension or gel comprising a crushed dosage form).

In certain embodiments, the irritant discourages contact with a mucosal membrane. In certain embodiments, the irritant discourages inhalation (e.g., oral or nasal) of the crushed dosage form by inducing pain and/or irritation of the abuser's mucous membrane and/or respiratory passageway tissue. In some of these embodiments, the irritant discourages inhalation (e.g., via breathing through the mouth or via snorting through the nose) by inducing pain and/or irritation of the abuser's respiratory (e.g., nasal or oral) passageway tissue.

In certain embodiments, the irritant may cause irritation of mucous membranes located anywhere on or in the body, including membranes of the mouth, eyes, nose and intestinal tract. Such compositions may deter abuse via oral, intraocular, rectal, or vaginal routes.

In certain embodiments, the irritant may comprise from about 1 to about 25%, from about 1% to about 15%, from about 3% to about 12%, from about 3% to about 10%, or from about 1% to about 5% of the dosage form by weight.

Suitable irritants for inclusion in the dosage form of the present invention include, e.g., surfactants (e.g., sodium lauryl sulfate, poloxamer, sorbitan monoesters, glyceryl monooleates, etc.), niacin, capsaicin, capsaicin analogs (e.g., resiniferatoxin, tinyatoxin, heptanoylisobutylamide, heptanoyl guaiacylamide, other isobutylamides or guaiacylamides, dihydrocapsaicin, homovanillyl octylester, nonanoyl vanillylamide), and mixtures thereof.

A suitable irritant may be of natural or synthetic origin and include, e.g., mustard, for example, allyl isothiocyaanate and p-hydroxybenzyl isothiocyanate; dihydrocapsaicin, nordihydrocapsaicin, homocapsaicin, and homodihydrocapsaicin; mint; aspirin; and acids such as acids with one or more carboxyl moieties such as formic acid, acetic acid, propionic acid, butyric acid, valeric acid, caproic acid, caprillic acid, capric acid, oxalic acid, malonic acid, succinic acid, glutaric acid, adipic acid, maleic acid, fumaric acid, and citric acid, etc.

In certain embodiments, the irritant is sodium lauryl sulfate.

In certain embodiments, the irritant is niacin.

In certain embodiments, the irritant is capsaicin.

In certain embodiments, the irritant is a surfactant.

In certain embodiments, the irritant may be included in the dosage form in a sequestered form. The sequestered form of the irritant may be prepared as described above in the section describing preparation of the sequestered form of the tonicity-increasing agent.

Bittering Agents

A dosage form of the present invention may include a bittering agent.

Bittering agents include compounds used to impart a bitter taste, bitter flavor, etc., to an abuser administering a tampered dosage form of the present invention. With the inclusion of a bittering agent in the formulation, the intake of the tampered dosage form produces a bitter taste upon inhalation or oral administration, which in certain embodiments will serve to spoil the pleasure of obtaining a high from the tampered dosage form, and preferably prevent the abuse of the dosage form.

A bittering agent may include, e.g., natural, artificial and synthetic flavor oils and flavoring aromatics and/or oils, oleoresins and extracts derived from plants, leaves, flowers, fruits, and so forth, and combinations thereof. Nonlimiting representative flavor oils include, e.g., spearmint oil, peppermint oil, eucalyptus oil, oil of nutmeg, allspice, mace, oil of bitter almonds, menthol and the like.

In certain embodiments, a bittering agent comprises an artificial, natural or synthetic fruit flavors such as, e.g., citrus oils including lemon, orange, lime, grapefruit, and fruit essences and so forth.

In certain embodiments, a bittering agent may comprise sucrose derivatives (e.g., sucrose octaacetate), chlorosucrose derivatives, quinine sulphate, and the like.

In certain embodiments, a bittering agent may comprise denatonium benzoate NF-Anhydrous, sold under the name Bitrex™ (Macfarlan Smith Limited, Edinburgh, UK).

A bittering agent, when included in the dosage form, generally comprises less than about 50%, less than about 10%, less than about 5% of the dosage form by weight. In certain embodiments, the bittering agent comprises from about 0.1 to 8 percent of the dosage form by weight.

In certain embodiments, the bittering agent may be included in a sequestered form. The sequestered form of a bittering agent may be prepared as described above in the section describing preparation of the sequestered form of the tonicity-increasing agent.

Surfactants

A dosage form of the present invention may include a surfactant. A surfactant may act as a gelling agent and/or as an irritant.

A surfactant may comprise from about 0.01% to about 90% of the dosage form by weight.

A suitable surfactant may be an anionic surfactant, a cationic surfactant, a nonionic surfactant, or an amphoteric surfactant.

A suitable surfactant may be selected from ethylene oxides, propylene oxides, copolymers of ethylene oxide and propylene oxide, polyoxyethylenes, polyoxypropelenes, copolymers of polyoxyethylene and polyoxypropylene, copolymers of polyoxyethylene/polypropylene, copolymers of polyoxyethylene/polybutylene, perfluoropolyether ammonium carboxylate, sulfates, alkyl sulfates, lauryl sulfates, alkyl sulfate salts, alkyl ether sulfates, alkylaryl ether sulfates, sulfated fats and oils, sulfated monoglycerides, sulfated alkanolamides, sulfonates, olefin sulfonates, alkylaryl sulfonates, polyether sulfonates, naphthalene sulfonates, phosphates, phosphate esters, alkyl phosphates, alkyl phosphate salts, alkyl ether phosphates, ammonium compounds, alkyl ammonium salts, alkyl trimethylammonium salts, amines and amides, alkyl amines, amine oxides, alkyl aminopropionates, alkanolamides, amido amines, silicones and silicates, alcohols, dimethicones, simethicone, silicates, sarcosines, lauryl sarcosines, cocoyl sarcosines, alcohols, ethoxylated alcohols, propoxylated alcohols, alkyl alcohols and blends, glycols, polyethylene glycols, acetylenic alcohol, ethers and ethoxylates, glycol ethers, ethoxylated glycerine, polyoxyethylene alkyl ethers, lanolin ethoxylates, octyl phenol, ethoxylates, nonyl phenol ethoxylates, oleic acid, ethoxylates, cocoamine ethoxylates, tallow amine, ethoxylates, stearic acid ethoxylates, fatty acid ethoxylates, ethoxylated sorbitan esters, esters, methyl esters and blends, sorbitan esters, sucrose esters, fatty acid esters, polyethylene glycol esters, glycerol esters, glycol esters, butyl and isopropyl esters, sulfosuccinate esters, sulfuric acid esters, alkyl carboxylates, alkyl ether carboxylates, lactylates, sarcosinates, organic acids, carboxylic acids, fatty acids, plant oils, sulfosuccinates, taurate salts, EDTAs, alkyl iminodipropionates, alkyl imidazoline derivatives, lanolin derivatives, protein derivatives, alkyl polyglycosides, alkyl oligosaccharides, cyclodextrins, lecithins, betaines, and sultaines.

In certain embodiments, the surfactant is sodium lauryl sulfate.

In certain embodiments, the surfactant may be included in a sequestered form. The sequestered form of the surfactant may be prepared as described above in the section describing preparation of the sequestered form of the tonicity-increasing agent.

Staining Agents

A dosage form of the present invention may include one or more tissue staining agents. The staining agent may deter abuse of dosage form by staining the tissues that come into contact with the staining agent.

In a preferred embodiment, the staining agent is not released until the dosage form is tampered with (e.g., crushed to a powder). After a dosage form is tampered with (e.g., by crushing), the staining agent is exposed and may stain tissues that contact the tissue staining agent. For example in certain embodiments, the fingers of an abuser can be stained upon touching a crushed dosage form of the present invention. In certain embodiments, the nose and/or area in or about the nose, or the oral cavity of an abuser can be stained upon inhalation or swallowing of a crushed dosage form of the present invention.

In certain embodiments, a tissue staining agent is a non-toxic colored dye. The staining agent may be a water-soluble dye or an oil-soluble dye.

In certain embodiments, the staining agent is mixed with the active agent and excipients during manufacture of the dosage form of the present invention.

In certain embodiments of the present invention, suitable tissue staining agents include one or more of the following: FD&C Blue No. 1, FD&C Blue No. 2, FD&C Blue No. 4, FD&C Blue No. 9, FD&C Green No. 3, FD&C Green No. 5, D&C Green No. 6, D&C Green No. 8, D&C Orange No. 4, D&C Orange No. 5, D&C Orange No. 10, D&C Orange No. 11, FD&C Red No. 3, FD&C Red No. 40, D&C Red No. 3, D&C Red No. 4, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Red No. 39, FD&C Yellow No. 5, FD&C Yellow No. 6, D&C Yellow No. 7, Ext. D&C Yellow No. 7, D&C Yellow No. 8, D&C Yellow No. 10, D&C Yellow No. 11, Orange B, Citrus Red No. 2, annatto extract, beta-carotene, canthaxanthin, alumina (dried aluminum hydroxide), chromium-cobalt-aluminum oxide, ferric ammonium citrate, calcium carbonate, caramel, cochineal extract, carmine, potassium sodium copper chloropyhllin (chrolophyllin-copper complex), dihydroxyacetone, bismuth oxychloride, synthetic iron oxide, ferric ammonium ferrocyanide, ferric ferrocyanide, chromium hydroxide green, chromium oxide greens, guanine, mica-based pearlescent pigments, pyrogallol, pyrophyllite, logwood extract, mica, talc, titanium dioxide, aluminum powder, bronze powder, copper powder, zinc oxide, and the like.

In certain embodiments, the present invention can include the dyes set forth in U.S. Patent Application Publication No. 20040228802, to Chang et al., herein incorporated by reference. Such dyes include allura red, amaranth, brilliant blue, canthaxanthin, carmine, carmoisine, carotene, curcumin, erythrosine, green S, indigo carmine, iron oxide black, iron oxide red, iron oxide yellow, patent blue, phloxine 0, ponceau 4R, quinoline yellow, riboflavin, sunset yellow, tartrazine, titanium dioxide, vegetable carbon black, and other natural colors such as annatto, beet, black carrot, black currant, caramel, carmine, carmine lake, chlorophyll, cochineal, elderberry, grapeskin/grape juice, malt, paprika, red cabbage, turmeric, and anthocyanins.

The amount of the dye used in a dosage form of the present invention will vary with the particular dye used but, typically, the dye indicator is used in an amount of about 0.01% to about 20% by weight and, preferably, from about 0.1% to about 10% by weight, and, most preferably, from about 0.1% to 5% by weight, based on the weight of a dosage form.

Laxatives

A dosage form of the present invention may include a laxative.

In certain embodiments, the laxative is included in an amount which is at least 2-3 times less than the amount required to induce diarrhea. Thus, diarrhea can be avoided if normal prescription directions are followed. However, if an overdose occurs by ingesting more than a prescribed quantity of a dosage form, the total amount of ingested laxative will, in certain embodiments, produce diarrhea.

A dosage form may include from about 5 mg to 500 mg of a laxative.

In certain embodiments, the laxative may be sodium dioctyl sulfosuccinate, calcium dioctyl sulfosuccinate or potassium dioctyl sulfosuccinate.

In certain embodiments, the laxative may be included in a sequestered form. A sequestered form may be prepared as described above in the section describing preparation of the sequestered form of the tonicity-increasing agent.

Antagonists of Active Agents Susceptible to Abuse

A dosage form of the present invention may include a pharmacological antagonist of the active agent susceptible to abuse. The antagonist of the active agent may be included in a releasable and/or a sequestered form.

For example, if the active agent susceptible to abuse is an opioid analgesic, the dosage form may include an opioid antagonist, in addition to the tonicity-increasing agent described above.

A suitable opioid antagonist may be selected from the group comprising naltrexone, naloxone, nalmephene, cyclazocine, levallorphan, pharmaceutically acceptable salts thereof and mixtures thereof. In certain embodiments, the antagonist is naloxone, a naloxone salt, naltrexone, a naltrexone salt, or a mixture of any of the foregoing.

In certain embodiments, the opioid antagonist is naltrexone or a salt thereof.

In certain embodiments, the opioid antagonist included in the dosage form is in a sequestered form. Preparation of the opioid antagonist in a sequestered form is described, e.g., in U.S. Pat. No. 6,696,088, herein incorporated by reference. The sequestered form of the opioid antagonist may also be prepared as described above in the section describing preparation of the tonicity-increasing agent in a sequestered form.

If the active agent susceptible to abuse is a benzodiazepine, the dosage form may include a benzodiazepine antagonist. A suitable benzodiazepine antagonist includes, e.g., flumazenil or a salt thereof. In certain embodiments, a sequestered form of a benzodiazepine antagonist is used. The sequestered form of the benzodiazepine antagonist may be prepared as described above in the section describing preparation of the tonicity-increasing agent in a sequestered form.

If the active agent susceptible to abuse is a barbiturate, the dosage form may include a barbiturate antagonist. In certain embodiments, a sequestered form of the barbiturate antagonist is used. The sequestered form of the barbiturate antagonist may be prepared as described above in the section describing preparation of the tonicity-increasing agent in a sequestered form.

If the active agent susceptible to abuse is a stimulant, the dosage form may include a stimulant antagonist. In certain embodiments, a sequestered form of the stimulant antagonist is used. The sequestered form of the stimulant antagonist may be prepared as described above in the section describing preparation of the tonicity-increasing agent in a sequestered form.

Emetics

A dosage form of the present invention may include an emetic. In certain embodiments, the emetic is a substance which induces the emesis only after a certain threshold amount is ingested.

An amount of the emetic included in the dosage form of the present invention is such that the emesis is induced only when a subject takes a dose that is more than 2 to 3 times higher than the dose recommended by the manufacture of the dosage form.

In certain embodiments, the emetic is zinc sulfate. Doses of zinc sulfate below about 600 mg (e.g., 500 mg or less, 400 mg or less, 300 mg or less, 200 mg or less, 100 mg or less, etc.) are unlikely to induce emesis when ingested; however doses of zinc sulfate from about 600 mg to about 2 grams or more cause emesis when ingested. In certain embodiments, the dosage form of the present invention comprises from about 10 mg to about 200 mg of zinc sulfate, or an equivalent amount of a different emetic.

In certain embodiments, the emetic be included in the dosage form in a sequestered form. A sequestered form may be prepared as described above in the section describing preparation of the sequestered form of the tonicity-increasing agent.

Excipients

In addition to the active agent, tonicity-increasing agents and one or more optional additional abuse-deterrent agents, the dosage form may include one or more additional excipients. Suitable excipients include, e.g., fillers, binders, insoluble polymers, disintegrants, lubricants, glidants, surfactants, effervescent bases, osmotically active agents, swelling agents, agents that slow the release of the active agent from the core, ion exchange resins, hydrophobic materials controlling the rate of release of the active agent from the dosage form, substances of a type and in an amount which will form a semi-solid or gel composition upon crushing, heating and/or exposure of the crushed dosage form to an aqueous medium (e.g., 10 ml distilled water), and the like.

Suitable fillers include, e.g., water-soluble, compressible carbohydrates such as sugars, which include, e.g., dextrose, sucrose, isomaltose, fructose, maltose, lactose, and polydextrose; sugar-alcohols including, e.g., mannitol, sorbitol, isomalt, maltitol, xylitol, and erythritol; starch hydrolysates including, e.g., dextrins, and maltodextrins, and the like; water insoluble, plastic deforming materials such as, e.g., microcrystalline cellulose or other cellulosic derivatives; water-insoluble brittle fracture materials such as, e.g., dicalcium phosphate, tricalcium phosphate and the like; and mixtures thereof. In certain embodiments, the filler may act as a tonicity-increasing agent as described herein above.

Suitable binders include, e.g., dry binders such as, e.g., polyvinyl pyrrolidone, hydroxypropylmethylcellulose, and the like; wet binders such as, e.g., water-soluble polymers, including hydrocolloids such as, e.g., alginates, agar, guar gum, locust bean, carrageenan, tara, gum arabic, tragacanth, pectin, gellan, maltodextrin, galactomannan, pustulan, laminarin, scleroglucan, gum arabic, inulin, pectin, whelan, rhamsan, zooglan, methylan, chitin, cyclodextrin, chitosan, polyvinyl pyrrolidone, cellulosics, starches, and the like; and derivatives and mixtures thereof. In certain embodiments, an oral dosage form in accordance with the present invention does not include, and is free from a binder.

Suitable disintegrants include, e.g., sodium starch glycolate, cross-linked polyvinylpyrrolidone, cross-linked carboxymethylcellulose, starches, microcrystalline cellulose, and the like, and mixtures thereof.

Suitable lubricants include, e.g., long chain fatty acids and their salts, such as magnesium stearate and stearic acid, talc, waxes, and the like, and mixtures thereof.

Suitable glidants include, e.g., colloidal silicon dioxide, and the like.

In certain embodiments, a surfactant or an effervescent base is included in the dosage form. The surfactant may be helpful in certain cases to overcome surface tension effects. Surfactants useful as release-modifying agents in the present invention can be anionic, cationic, nonionic, and/or amphoteric. For example, sodium lauryl sulfate, sodium dodecyl sulfate, sorbitan esters, polysorbates, pluronics, potassium laurate, and the like, may be included in the dosage form.

In certain embodiments, one or more osmotically active agents or osmagents may be included in the dosage form. Osmagents are formulated such that they are not released when an intact dosage form is placed in 10 ml of distilled water but remain exposed to the fluid entering an intact dosage form. Osmagents are particularly useful when the active agent has limited solubility in the environment of use. In certain embodiments (e.g., when the osmagents are included inside a core coated with a semipermeable membrane (permeable to aqueous fluids, but impermeable to the active agent)), osmagents may facilitate diffusion of aqueous fluids inside of the core, thereby increasing a rate of dissolution of the active agent and release of the active agent from the core. In other embodiments (e.g., when the osmagents are included inside the core of a multi-layer dosage form), these agents may reduce internal pressure in the dosage form, thereby improving the structural stability/integrity of the dosage form.

Osmagents useful as release-modifying agents in the present invention include, for example, sodium chloride, calcium chloride, calcium lactate, sodium sulfate, lactose, glucose, sucrose, mannitol, urea, and other organic and inorganic compounds known in the art.

In certain embodiments, the dosage form includes one or more swelling agents provided in an amount sufficient to facilitate release of the active agent(s) from the dosage form, without causing uncontrolled disruption of the coating(s) surrounding the core. In these embodiments, upon exposure of the dosage to an aqueous medium, the swelling agent will swell and "push" the active agent(s) or a solution thereof out from the dosage form through a passageway in the coating(s) surrounding the dosage form. In certain embodiments, the passageway is formed by "laser drilling" of the coating or mantle. In certain other embodiments, the passageway is formed by selective cross-linking of the hydrogel in the coating or mantle of the dosage form, rather than being "laser-drilled."

Examples of suitable swelling agents include synthetic gums such as hydroxypropylmethylcelluloses (HPMC), hydroxypropyl cellulose (HPC), carboxymethyl cellulose, and natural gums such as locust bean gum, acacia, tragacanth, guar gum, carrageenan, and propylene glycol alginate.

The dosage form may also include agents which slow the release of active agent from the dosage form. Examples of such agents include hydrophobic materials and insoluble polymers. Examples of suitable hydrophobic materials useful as release-modifying agents include vegetable oils such as hydrogenated cottonseed oil, hydrogenated castor oil, and the like, poly(meth)acrylates and cellulosic materials, and mixtures of any of the foregoing.

The dosage form may also include one or more ion exchange resins.

Effervescent bases useful as release-modifying agents in the present invention include sodium glycine carbonate, sodium carbonate, potassium carbonate, sodium bicarbonate, potassium bicarbonate, calcium bicarbonate, and the like.

Other release-modifying agents which may be useful in the present invention provide a soluble or insoluble polymer backbone to the dosage form. Such agents may decrease unequal density areas of the dosage form formed during the compression molding of the same. Suitable soluble polymers which may be incorporated into the dosage form include those which melt upon compression and fuse upon cooling to provide nearly uniform cross-sectional density, such as polyethylene glycols having a molecular weight of from about 900 to about 20,000 daltons. Other water soluble polymers are those that can become sufficiently viscous upon contacting an aqueous fluid to provide the same effect, such as high molecular weight polyvinylpyrollidone (e.g., K90 grade, commercially available from GAF Corporation and having a molecular weight of about 360,000).

Excipients generally comprise from about 5 to about 98%, from about 55% to about 99.9% or from about 55% to about 97% of the dosage form by weight.

In certain embodiments, the active agent is dispersed in a matrix comprising polyethylene oxide(s).

In certain embodiments, the dosage form comprises hydroxyl alkylcellulose (e.g., hydroxypropyl cellulose) and/or microcrystalline cellulose. In certain embodiments, hydroxylpropyl cellulose comprises from about 0.1% to about 7% by weight of the dosage form, or from about 0.2% to about 6% by weight of the dosage form, or from about 0.2% to about 5% by weight of the dosage form. In certain embodiments, microcrystalline cellulose comprises from about 0.1% to about 7% by weight of the dosage form, or from about 0.2% to about 6% by weight of the dosage form, or from about 0.2% to about 5% by weight of the dosage form.

In certain embodiments, the core of the dosage form consists essentially of an active agent, polyethylene oxide and a lubricant. As used herein, the phrase "consists essentially of" means that the active agent, polyethylene oxide and the lubricant comprise more than 99% of the dosage form by weight. In certain embodiments, polyethylene oxide comprises from about 70% to about 95% or from about 75% to about 95% or from about 80% to about 95% of the dosage form by weight. In certain embodiments, the lubricant is magnesium stearate. In certain embodiments, the core comprises magnesium stearate in an amount of from about 0.1% to about 5%, or from about 0.1% to about 2%, or from about 0.2% to about 1% by weight of the core.

In certain embodiments, the dosage form comprises a material selected from the group consisting of polyethylene oxide, hydroxypropyl cellulose, hydroxypropyl methylcellulose, hydroxyethyl cellulose, microcrystalline cellulose, polycaprolactone, glyceryl behenate, magnesium stearate, and mixtures thereof.

The oral dosage forms of the present invention may or may not include an antioxidant. In the embodiment of the present invention wherein the oral dosage form includes an antioxidant, the antioxidant may increase stability of the dosage form, e.g., by preventing or slowing down the rate of degradation of the active agent(s).

Dosage Forms and Preparation Thereof

A combination of an active agent susceptible to abuse, a tonicity-increasing agent and one or more excipients may be formulated as an immediate release formulation and/or a controlled/sustained release formulation in any suitable tablet, coated tablet or multiparticulate formulation (e.g., capsule), transdermal delivery system, and/or suppository known to those skilled in the pharmaceutical arts.

The sustained release dosage form may comprise a matrix comprising (i) a sustained release carrier, (ii) an active agent susceptible to abuse and (iii) a tonicity-increasing agent in the immediate release form, sustained release form and/or sequestered form.

In certain embodiments, the sustained release dosage form comprises a plurality of particles of an active agent susceptible to abuse (e.g., an opioid agonist), wherein the particles have diameter from about 0.1 mm to about 2.5 mm, preferably from about 0.5 mm to about 2 mm. The particles may be film-coated with a material that permits release of the active agent susceptible to abuse at a sustained rate in an aqueous medium (e.g., distilled water) for about 8 to 24 hours. The film coat is chosen so as to achieve, in combination with the other stated properties, a desired in-vitro release rate. The sustained release coating formulations of the present invention should be capable of producing a strong, continuous film that is smooth and elegant, capable of supporting pigments and other coating additives, non-toxic, inert, and tack-free.

The dosage form comprising a core comprising an active agent susceptible to abuse and a tonicity-increasing agent may optionally be coated with one or more materials suitable for the regulation of release of the active agent susceptible to abuse and/or for the protection of the formulation. In one embodiment, coatings are provided to permit either pH-dependent (e.g., when exposed to gastrointestinal fluid) or pH-independent release.

A pH-dependent coating serves to release the active agent susceptible to abuse in desired areas of the gastro-intestinal (GI) tract, e.g., the stomach or small intestine. When a pH-independent coating is desired, the coating is designed to achieve optimal release of the active agent regardless of pH-changes in the GI tract. It is also possible to formulate compositions which release a first portion of the dose in one desired area of the GI tract, e.g., the stomach, and then release a second portion of the dose in another area of the GI tract, e.g., the small intestine.

Formulations according to the invention that utilize pH-dependent coatings to obtain formulations may also impart a repeat-action effect whereby active agent in an immediate release form is coated over the enteric coat and is released in the stomach, while the remainder, being protected by the enteric coating, is released further down the gastrointestinal tract. pH-Dependent coatings that may be used in accordance with the present invention include shellac, cellulose acetate phthalate (CAP), polyvinyl acetate phthalate (PVAP), hydroxypropylmethylcellulose phthalate, and methacrylic acid ester copolymers, zein, and the like.

In certain preferred embodiments, the substrate (e.g., tablet core bead, matrix particle) containing the active agent and the tonicity-increasing agent is coated with a hydrophobic material selected from (i) an alkylcellulose; (ii) an acrylic polymer; or (iii) mixtures thereof. The coating may be applied in the form of an organic or aqueous solution or dispersion. The coating may be applied to obtain a weight gain from about 2 to about 25% of the substrate in order to obtain a desired sustained release profile. Coatings derived from aqueous dispersions are described, e.g., in detail in U.S. Pat. Nos. 5,273,760 and 5,286,493, hereby incorporated by reference.

Other examples of sustained release formulations and coatings which may be used in accordance with the present invention are described in U.S. Pat. Nos. 5,324,351; 5,356,467, and 5,472,712, which are hereby incorporated by reference in their entirety.

Alkylcellulose Polymers

Cellulosic materials and polymers, including hydrophobic alkylcelluloses, may be used as hydrophobic materials in the controlled release coatings or controlled release matrices useful according to the present invention. Simply by way of example, one preferred alkylcellulosic polymer is ethylcellulose, although other cellulose and/or alkylcellulose polymers may be readily employed, singly or in any combination, as all or part of a hydrophobic coating or matrix according to the invention.

One commercially-available aqueous dispersion of ethylcellulose is Aquacoat® (FMC Corp., Philadelphia, Pa., U.S.A.), which is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion that can be applied directly onto substrates.

Acrylic Polymers

In certain embodiments, the hydrophobic materials that may be incorporated into a controlled release coating or a controlled release matrix in accordance with the present invention include, e.g., a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers, among others.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In order to obtain a desirable dissolution profile, it may be necessary to incorporate two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the present invention. For example, there is a family of copolymers synthesized from diethylaminoethyl methacrylate and other neutral methacrylic esters, also known as methacrylic acid copolymer or polymeric methacrylates, commercially available as Eudragit® from Evonik.

There are several different types of Eudragit®. For example, Eudragit® E is an example of a methacrylic acid copolymer which swells and dissolves in acidic media. Eudragit® L is a methacrylic acid copolymer which does not swell at about pH<5.7 and is soluble at about pH>6. Eudragit® S does not swell at about pH<6.5 and is soluble at about pH>7. Eudragit® RL and Eudragit® RS are water swellable, and the amount of water absorbed by these polymers is pH-dependent, however, dosage forms coated with Eudragit® RL and RS are pH-independent.

In certain preferred embodiments, the acrylic coating comprises a mixture of two acrylic resin lacquers commercially available from Evonik under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a sustained release formulation having a desirable dissolution profile. Desirable sustained release formulations may be obtained, for instance, from a retardant coating derived from 100% Eudragit® RL, 50% Eudragit® RL and 50% Eudragit® RS, and 10% Eudragit® RL and 90% Eudragit® RS. Of course, one skilled in the art will recognize that other acrylic polymers may also be used, such as, for example, Eudragit® L.

Plasticizers

In embodiments of the present invention where the coating comprises an aqueous dispersion of a hydrophobic material, the inclusion of an effective amount of a plasticizer in the aqueous dispersion of hydrophobic material will further improve the physical properties of the sustained release coating. For example, because ethylcellulose has a relatively high glass transition temperature and does not form flexible films under normal coating conditions, it is preferable to incorporate a plasticizer into an ethylcellulose coating containing sustained release coating before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

It has further been found that the addition of a small amount of talc reduces the tendency of the aqueous dispersion to stick during processing, and acts as a polishing agent.

Processes for Preparing Coated Beads

When a hydrophobic controlled release coating material is used to coat inert pharmaceutical beads such as nu pariel 18/20 beads, which are already coated with an active agent and a tonicity-increasing agent, a plurality of the resultant solid controlled release beads may thereafter be placed in a gelatin capsule. The dosage form provides an effective controlled release dose of the active agent when ingested orally intact and contacted by an environmental fluid, e.g., gastric fluid. In certain embodiments, particles of tonicity-increasing agent in a sequestered form are also included in the gelatin capsule.

The controlled release bead formulations of the present invention slowly release the active agent (e.g., opioid agonist), e.g., when ingested orally intact and exposed to gastric fluids, and then to intestinal fluids.

The controlled release profile of the formulations of the invention can be altered, for example, by varying the amount of hydrophobic material in one or more coatings, altering the manner in which the plasticizer is added to the hydrophobic material, by varying the amount of plasticizer relative to hydrophobic material, by the inclusion of additional excipients (e.g., ionic surfactants (e.g., sodium lauryl sulfate), by altering the method of manufacture, etc. The dissolution profile of the ultimate product may also be modified, for example, by increasing or decreasing the thickness of the retardant coating.

Spheroids or beads coated with an agent may be prepared, e.g., by dissolving the active agent in water and then spraying the solution onto a substrate, for example, nu panel 18/20 beads, using a Wuster insert. Optionally, additional excipients may be added prior to coating the beads in order to assist the binding of the active agent to the beads, and/or to color the solution, etc. For example, a product which includes hydroxypropylmethylcellulose, etc. with or without colorant (e.g., Opadry®, commercially available from Colorcon, Inc.) may be added to the solution and the solution mixed (e.g., for about 1 hour) prior to application of the same onto the beads. The resultant coated substrate, in this example beads, may then be optionally overcoated with a barrier agent, to separate the therapeutically active agent from the hydrophobic controlled release coating. An example of a suitable barrier agent is one which comprises hydroxypropylmethylcellulose. However, any film-former known in the art may be used. It is preferred that the barrier agent does not affect the dissolution rate of the final product.

The beads may then be overcoated with an aqueous dispersion of the hydrophobic material. The aqueous dispersion of hydrophobic material preferably further includes an effective amount of plasticizer, e.g. triethyl citrate. Preformulated aqueous dispersions of ethylcellulose, such as Aquacoat® or Surelease®, may be used. If Surelease® is used, it is not necessary to separately add a plasticizer. Alternatively, pre-formulated aqueous dispersions of acrylic polymers such as Eudragit® can be used.

The coating solutions of the present invention preferably contain, in addition to the film-former, plasticizer, and solvent system (i.e., water), a colorant to provide elegance and product distinction. Color may be added to the solution of the therapeutically active agent instead, or in addition to the aqueous dispersion of hydrophobic material. For example, color may be added to Aquacoat® via the use of alcohol or propylene glycol based color dispersions, milled aluminum lakes and opacifiers such as titanium dioxide by adding color with shear to water soluble polymer solution and then using low shear to the plasticized Aquacoat®. Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments. The incorporation of pigments, may, however, increase the retard effect of the coating.

Plasticized hydrophobic material may be applied onto the substrate comprising the active agent by spraying using any suitable spray equipment known in the art. In a preferred method, a Wurster fluidized-bed system is used in which an air jet, injected from underneath, fluidizes the core material and effects drying while the acrylic polymer coating is sprayed on. A sufficient amount of the hydrophobic material to obtain a predetermined controlled release of said therapeutically active agent when the coated substrate is exposed to aqueous solutions, e.g. gastric fluid, is preferably applied, taking into account the physical characteristics of the therapeutically active agent, the manner of incorporation of the plasticizer, etc. After coating with the hydrophobic material, a further overcoat of a film-former, such as Opadry®, is optionally applied to the beads. This overcoat is provided, if at all, in order to substantially reduce agglomeration of the beads.

The release of the active agent from the controlled release formulation of the present invention can be further influenced, i.e., adjusted to a desired rate, by the addition of one or more release-modifying agents, or by providing one or more passageways through the coating. The ratio of hydrophobic material to water soluble material is determined by, among other factors, the release rate required and the solubility characteristics of the materials selected.

The release-modifying agents which function as pore-formers may be organic or inorganic, and include materials that can be dissolved, extracted or leached from the coating in the environment of use. The pore-formers may comprise one or more hydrophilic materials such as hydroxypropylmethylcellulose.

The sustained release coatings of the present invention can also include erosion-promoting agents such as starch and gums.

The sustained release coatings of the present invention can also include materials useful for making microporous lamina in the environment of use, such as polycarbonates comprised of linear polyesters of carbonic acid in which carbonate groups reoccur in the polymer chain.

The release-modifying agent may also comprise a semipermeable polymer.

In certain preferred embodiments, the release-modifying agent is selected from hydroxypropylmethylcellulose, lactose, metal stearates, and mixtures of any of the foregoing.

The sustained release coatings of the present invention may also include an exit means comprising at least one passageway, orifice, or the like. The passageway may be formed by such methods as those disclosed in U.S. Pat. Nos. 3,845,770; 3,916,889; 4,063,064; and 4,088,864 (all of which are hereby incorporated by reference). The passageway can have any shape such as round, triangular, square, elliptical, irregular, etc.

Matrix Formulations

In other embodiments of the present invention, the controlled release formulation is achieved via a matrix having a controlled release material as set forth above.

In certain embodiments, the dosage form comprises a sustained release tablet comprising (i) an active agent susceptible to abuse (e.g., an opioid agonist) and (ii) a tonicity-increasing agent in immediate release form, sustained release form or sequestered form dispersed in a controlled release material as set forth above.

In addition to the controlled release materials mentioned above, the active agent and the tonicity-increasing agent, the matrix may include:

Hydrophilic and/or hydrophobic materials, such as gums, cellulose ethers, acrylic resins, protein derived materials; the list is not meant to be exclusive, and any pharmaceutically acceptable hydrophobic material or hydrophilic material which is capable of imparting controlled release of the active agent may be used in accordance with the present invention.

Digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and waxes, and stearyl alcohol; and polyalkylene glycols.

In certain embodiments, the hydrophobic material in the matrix comprises an acrylic polymer (e.g., Eudragit® RSPO), cellulose ethers, a hydroxyalkylcelluloses, a carboxyalkylcelluloses, or a mixture of any of the foregoing.

The dosage form may contain between 1% and 80% (by weight) of at least one hydrophilic or hydrophobic material.

When the hydrophobic material is a hydrocarbon, the hydrocarbon preferably has a melting point of between 25° and 90° C. Of the long chain hydrocarbon materials, fatty (aliphatic) alcohols are preferred. The oral dosage form may contain up to 60% (by weight) of at least one digestible, long chain hydrocarbon.

The oral dosage form may contain up to 70% (by weight) of at least one polyalkylene glycol.

The hydrophobic material for inclusion in the matrix or a coating may also be selected from the group consisting of alkylcelluloses, acrylic and methacrylic acid polymers and copolymers, shellac, zein, hydrogenated castor oil, hydrogenated vegetable oil, or mixtures thereof. In certain embodiments of the present invention, the hydrophobic material is a pharmaceutically acceptable acrylic polymer, including but not limited to acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer, poly(methyl methacrylate), poly(methacrylic acid)(anhydride), polymethacrylate, polyacrylamide, poly(methacrylic acid anhydride), and glycidyl methacrylate copolymers. In other embodiments, the hydrophobic material is selected from materials such as hydroxyalkylcelluloses such as hydroxypropylmethylcellulose and mixtures of the foregoing.

In certain embodiments, hydrophobic materials are water-insoluble with more or less pronounced hydrophilic and/or hydrophobic trends. Preferably, the hydrophobic materials useful in the invention have a melting point from about 30° to about 200° C., preferably from about 45° to about 90° C. Specifically, the hydrophobic material may comprise natural or synthetic waxes, fatty alcohols (such as lauryl, myristyl, stearyl, cetyl or preferably cetostearyl alcohol), fatty acids, including but not limited to fatty acid esters, fatty acid glycerides (mono-, di-, and tri-glycerides), hydrogenated fats, hydrocarbons, normal waxes, stearic acid, stearyl alcohol and hydrophobic and hydrophilic materials having hydrocarbon backbones. Suitable waxes include, for example, beeswax, glycowax, castor wax and carnauba wax. For purposes of the present invention, a wax-like substance is defined as any material which is normally solid at room temperature and has a melting point of from about 30° to about 100° C.

Suitable hydrophobic materials which may be used in accordance with the present invention also include digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and natural and synthetic waxes. Hydrocarbons having a melting point of between 25° and 90° C. are preferred. Of the long chain hydrocarbon materials, fatty (aliphatic) alcohols are preferred in certain embodiments. The oral dosage form may contain up to 60% (by weight) of at least one digestible, long chain hydrocarbon.

In certain embodiments, a combination of two or more hydrophobic materials is included in the matrix formulations. If an additional hydrophobic material is included, it is may be selected from natural and synthetic waxes, fatty acids, fatty alcohols, and mixtures of the same. Examples include beeswax, carnauba wax, stearic acid and stearyl alcohol. This list is not meant to be exclusive.

One particular suitable matrix comprises at least one water-soluble hydroxyalkyl cellulose, at least one $C_{12}$-$C_{36}$, preferably $C_{14}$-$C_{22}$, aliphatic alcohol and, optionally, at least one polyalkylene glycol. The at least one hydroxyalkyl cellulose is preferably a hydroxy ($C_1$ to $C_6$) alkyl cellulose, such as hydroxypropylcellulose, hydroxypropylmethylcellulose and, especially, hydroxyethylcellulose. The amount of the at least one hydroxyalkyl cellulose in the present oral dosage form will be determined, inter alia, by the precise rate of active agent release required. The at least one aliphatic alcohol may be, for example, lauryl alcohol, myristyl alcohol or stearyl alcohol. In certain embodiments of the present oral dosage form, however, the at least one aliphatic alcohol is cetyl alcohol or cetostearyl alcohol. The amount of the at least one aliphatic alcohol in the present oral dosage form will be determined, as above, by the precise rate of active agent release required. It will also depend on whether at least one polyalkylene glycol is present in or absent from the oral dosage form. In the absence of at least one polyalkylene glycol, the oral dosage form may contain between 20% and 50% (by weight) of the at least one aliphatic alcohol. When at least one polyalkylene glycol is present in the oral dosage form, then the combined weight of the at least one aliphatic alcohol and the at least one polyalkylene glycol may constitute between 20% and 50% (by weight) of the total dosage.

In one embodiment, the ratio of, e.g., the at least one hydroxyalkyl cellulose or acrylic resin to the at least one aliphatic alcohol/polyalkylene glycol determines, to a considerable extent, the release rate of the opioid from the formulation. A ratio of the at least one hydroxyalkyl cellulose to the at least one aliphatic alcohol/polyalkylene glycol of between 1:2 and 1:4 is preferred, with a ratio of between 1:3 and 1:4 being particularly preferred.

The at least one polyalkylene glycol may be, for example, polypropylene glycol or, which is preferred, polyethylene glycol. The number average molecular weight of the at least one polyalkylene glycol is preferred between 1,000 and 15,000 especially between 1,500 and 12,000.

Another suitable controlled release matrix may comprise an alkylcellulose (especially ethyl cellulose), a $C_{12}$ to $C_{36}$ aliphatic alcohol and, optionally, a polyalkylene glycol.

In another preferred embodiment, the matrix includes a pharmaceutically acceptable combination of at least two hydrophobic materials.

In addition to the above ingredients, a controlled release matrix may also contain suitable quantities of other materials, e.g. diluents, lubricants, binders, granulating aids, colorants, flavorants and glidants that are conventional in the pharmaceutical art.

Processes for Preparing Matrix-Based Beads

In order to facilitate the preparation of a solid, controlled release, oral dosage form according to this invention, any method of preparing a matrix formulation known to those skilled in the art may be used. For example incorporation in the matrix may be effected, for example, by (a) forming granules comprising at least one water soluble hydroxyalkyl cellulose, active agent and one or more tonicity-increasing agents; (b) mixing the hydroxyalkyl cellulose containing granules with at least one $C_{12}$-$C_{36}$ aliphatic alcohol; and (c) optionally, compressing and shaping the granules. Preferably, the granules are formed by wet granulating the hydroxy-alkyl cellulose/opioid with water. In particular embodiment of this process, the amount of water added during the wet granulation step is between 1.5 and 5 times, especially between 1.75 and 3.5 times, the dry weight of the active agent.

In yet other alternative embodiments, a spheronizing agent, together with the active ingredient and one or more tonicity-increasing agent can be spheronized to form spheroids. Microcrystalline cellulose is preferred. A suitable microcrystalline cellulose is, for example, the material sold as Avicel PH 101 (Trade Mark, FMC Corporation). In such embodiments, in addition to the active ingredient and spheronizing agent, the spheroids may also contain a binder. Suitable binders, such as low viscosity, water soluble polymers, will be well known to those skilled in the pharmaceutical art. However, water soluble hydroxy lower alkyl cellulose, such as hydroxypropylcellulose, is preferred. Additionally (or alternatively) the spheroids may contain a water insoluble polymer, especially an acrylic polymer, an acrylic copolymer, such as a methacrylic acid-ethyl acrylate copolymer, or ethyl cellulose. In such embodiments, the sustained release coating will generally include a hydrophobic material such as (a) a wax, either alone or in admixture with a fatty alcohol; or (b) shellac or zein.

Melt Extrusion Matrix

Sustained release matrices can also be prepared via melt-granulation or melt-extrusion techniques, as long as the techniques used do not damage the integrity of the sequestered abuse-deterrent agent(s) added during the preparation of the matrix to the extent that sufficient amount of the abuse-deterrent agent(s) becomes available to be released into the gastrointestinal system upon oral administration. Alternatively, the melt extrusion step may be performed with the active agent (e.g., opioid agonist) to produce sustained release particles of the active agent, which may then be combined with the tonicity-increasing agent in immediate release form, sustained release form or sequestered form.

Generally, melt-granulation techniques involve melting a normally solid hydrophobic material, e.g. a wax, and incorporating a powdered active agent and one or more tonicity increasing agent(s) therein. To obtain a sustained release dosage form, it may be necessary to incorporate an additional hydrophobic substance, e.g. ethylcellulose or a water-insoluble acrylic polymer, into the molten wax hydrophobic material. Examples of sustained release formulations prepared via melt-granulation techniques are found in U.S. Pat. No. 4,861,598, hereby incorporated by reference in its entirety.

The additional hydrophobic material may comprise one or more water-insoluble wax-like thermoplastic substances possibly mixed with one or more wax-like thermoplastic substances being less hydrophobic than said one or more water-insoluble wax-like substances. In order to achieve constant release, the individual wax-like substances in the formulation should be substantially non-degradable and insoluble in gastrointestinal fluids during the initial release phases. Useful water-insoluble wax-like substances may be those with a water-solubility that is lower than about 1:5,000 (w/w).

In addition to the above ingredients, a sustained release matrix may also contain suitable quantities of other materials, e.g., diluents, lubricants, binders, granulating aids, colorants, flavorants and glidants that are conventional in the pharmaceutical art. The quantities of these additional materials will be sufficient to provide the desired effect to the desired formulation.

In addition to the above ingredients, a sustained release matrix incorporating melt-extruded multiparticulates may also contain suitable quantities of other materials, e.g. diluents, lubricants, binders, granulating aids, colorants, flavorants and glidants that are conventional in the pharmaceutical art in amounts up to about 50% by weight of the particulate if desired.

Specific examples of pharmaceutically acceptable carriers and excipients that may be used to formulate oral dosage forms are described in the Handbook of Pharmaceutical Excipients, American Pharmaceutical Association (1986), incorporated by reference herein.

Melt Extrusion Multiparticulates

The preparation of a suitable melt-extruded matrix according to the present invention may, for example, include the steps of blending the active agent (e.g., opioid analgesic), one or more tonicity-increasing agent(s), together with at least one hydrophobic material and preferably the additional hydrophobic material to obtain a homogeneous mixture. The homogeneous mixture is then heated to a temperature sufficient to at least soften the mixture sufficiently to extrude the same. The resulting homogeneous mixture is then extruded to form strands. The extrudate is preferably cooled and cut into multiparticulates by any means known in the art. The strands are cooled and cut into multiparticulates. The multiparticulates are then blended with the opioid antagonist particles coated with a coating that renders the antagonist substantially non-releasable and divided into unit doses. The extrudate preferably has a diameter of from about 0.1 to about 5 mm and provides sustained release of the active agent for a time period of from about 8 to about 24 hours.

An optional process for preparing the melt extrusions of the present invention includes directly metering into an extruder a hydrophobic material, an active agent, one or more tonicity-increasing agent(s) and an optional binder; heating the homogenous mixture; extruding the homogenous mixture to thereby form strands; cooling the strands containing the homogeneous mixture; cutting the strands into particles having a size from about 0.1 mm to about 12 mm; and combining the particles with the tonicity-increasing agent particles and dividing them into unit doses. In this aspect of the invention, a relatively continuous manufacturing procedure is realized.

The diameter of the extruder aperture or exit port can also be adjusted to vary the thickness of the extruded strands. Furthermore, the exit part of the extruder need not be round; it can be oblong, rectangular, etc. The exiting strands can be reduced to particles using a hot wire cutter, guillotine, etc.

The melt extruded multiparticulate system can be, for example, in the form of granules, spheroids or pellets depending upon the extruder exit orifice. For purposes of the present invention, the terms "melt-extruded multiparticulate(s)" and "melt-extruded multiparticulate system(s)" and "melt-extruded particles" shall refer to a plurality of units, preferably within a range of similar size and/or shape and containing one or more active agents and one or more excipients, preferably including a hydrophobic material as described herein. In this regard, the melt-extruded multiparticulates will be of a range of from about 0.1 to about 12 mm in length and have a diameter of from about 0.1 to about 5 mm. In addition, it is to be understood that the melt-extruded multiparticulates can be any geometrical shape within this size range. Alternatively, the extrudate may simply be cut into desired lengths and divided into unit doses of the active agent without the need of a spheronization step.

In one preferred embodiment, oral dosage forms are prepared to include an effective amount of melt-extruded multiparticulates within a capsule. For example, a plurality of the melt-extruded multiparticulates may be placed in a gelatin capsule in an amount sufficient to provide an effective sustained release dose when ingested and contacted by gastric fluid.

In another preferred embodiment, a suitable amount of the multiparticulate extrudate is combined with the tonicity-increasing agent and compressed into an oral tablet using conventional tableting equipment using standard techniques. Techniques and compositions for making tablets (compressed and molded), capsules (hard and soft gelatin) and pills are also described in Remington's Pharmaceutical Sciences, (Arthur Osol, editor), 1553-1593 (1980), incorporated by reference herein.

In yet another preferred embodiment, particles of the tonicity-increasing agent are added during the extrusion process and the extrudate can be shaped into tablets as set forth in U.S. Pat. No. 4,957,681 (Klimesch, et al.), described in additional detail above and hereby incorporated by reference.

Optionally, the sustained release melt-extruded multiparticulate systems or tablets can be coated, or the gelatin capsule can be further coated, with a sustained release coating such as the sustained release coatings described above. Such coatings preferably include a sufficient amount of hydrophobic material to obtain a weight gain level from about 2 to about 30 percent, although the overcoat may be greater depending upon the physical properties of the particular active agent utilized and the desired release rate, among other things.

The melt-extruded unit dosage forms of the present invention may further include combinations of melt-extruded multiparticulates containing one or more of the active agents disclosed above before being encapsulated. Furthermore, the unit dosage forms can also include an amount of an immediate release active agent (e.g., opioid agonist) for prompt therapeutic effect. The immediate release active agent (e.g., opioid agonist) may be incorporated, e.g., as separate pellets within a gelatin capsule, or may be coated on the surface of the multiparticulates after preparation of the dosage forms (e.g., controlled release coating or matrix-based). The unit dosage forms of the present invention may also contain a combination of controlled release beads and matrix multiparticulates to achieve a desired effect.

The sustained release formulations of the present invention preferably slowly release the active agent, e.g., when ingested and exposed to gastric fluids, and then to intestinal fluids. The sustained release profile of the melt-extruded formulations of the invention can be altered, for example, by varying the amount of retardant, i.e., hydrophobic material, by varying the amount of plasticizer relative to hydrophobic material, by the inclusion of additional ingredients or excipients, by altering the method of manufacture, etc.

Mini-Tablets

Dosage forms of the present invention may be prepared as mini-tablets. Mini-tablets are tablets which are smaller than conventional tablets but larger than conventional powder particles put in a conventional capsule. A plurality of mini-tablets is usually placed in a gelatin capsule.

Each mini-tablet is generally from about 2 to about 4 mm in diameter. Conventional powder particles put in a conventional capsule are about from about 100 to about 600 microns in diameter.

Mini-tablets generally provide an immediate release of the active agent. However, mini-tablets may also provide a sustained release of the active agent. In certain embodiments, the active agent is an opioid analgesic (e.g., oxycodone, hydrocodone, morphine, hydromorphone, a pharmaceutically acceptable salt of any of the foregoing, etc.).

Mini-tablets typically provide more surface area than conventional tablets, and, in certain embodiments, may provide for ability to adjust/control the release rate more easily. As compared to the conventional tablets, the mini-tablets may also be more tamper resistant, because the multi-tablets are smaller in size and are more difficult to crush.

Mini-tablets may also provide an opportunity to include "abuse-deterrent agents" in the dosage form more easily (e.g., because of a reduced size constraints).

With immediate release mini-tablets comprising an active agent susceptible to abuse (e.g., an opioid agonist), an abuser may crush a number of mini-tablets (e.g., 2-3 times a conventional dose), and/or snore the crushed powder or dissolve the crushed powder in water and inject the resulting solution or suspension.

Inclusion of one or more tonicity-increasing agent(s) in a mini-tablet, e.g., ensures, that the resulting solution or suspension is hypertonic and that, if injected intravenously, will cause pain and discomfort at the injection site.

The amount of the tonicity-increasing agent in the mini-tablet is such that if the capsule comprising mini-tablets is taken orally as intended by the manufacturer and in the amount intended by the manufacturer, it will not cause discomfort to a person taking it. However, if the mini-tablets are dissolved and injected (e.g., intravenously) or crushed and snored, in the preferred embodiments, the person will experience pain or burning at the site of the injection or contact of the crushed mini-tablets with a nasal mucosal membrane. The pain or burning will preferably be sufficient to deter the person from injecting or snorting the mini-tablets.

In certain embodiments, the amount of the tonicity-increasing agent in a mini-tablet is from 2 to 5 or from 2 to 3 times less than the amount required to provide a solution, suspension or gel with an osmolality which causes pain or burning sufficient to deter abuse when a crushed mini-tablet contacts an oral and/or nasal mucosal membrane of a subject or is dissolved in about from about 1 ml to about 10 ml or from about 2 ml to about 5 ml of distilled water and injected intravenously. This way, when an abuser attempts to crush a number of mini-tablets (e.g., from 2 to 3 or from 2 to 5 mini-tablets) and snore the crushed powder and/or dissolve the crushed powder in water and inject the resulting solution, suspension, or gel, the abuser will preferably experience pain and/or burning at the contact or the injection site. The pain or burning will preferably be sufficient to deter the person from injecting or snorting the mini-tablets. In these embodiments, each mini-tablet comprises an amount of an opioid analgesic, benzodiazepine, barbiturate or a stimulant which is insufficient to cause a euphoric feeling in the abuser or satisfy the cravings of the abuser.

Mini-tablets may be manufactured using convention equipment (e.g., high shear mixer, V-blender, rotary tablet press, tablet coated).

In certain embodiments, mini-tablets are manufactured by direct compression using, e.g., "multi-tip" tooling.

In certain embodiments, an active agent susceptible to abuse and one or more tonicity-increasing agent(s) are compressed into a mini-tablet by direct compression.

In certain embodiments, an active agent susceptible to abuse, a gelling agent (e.g., polyethylene oxide), and on optional flowing agent (e.g., talc, magnesium stearate, silicified cellulose, etc.) are compressed into mini-tablet by direct compression.

In certain embodiments, an active agent susceptible to abuse and a tonicity-increasing agent, along with optional additional abuse-deterrent agents, and one or more excipients are blended together, and then comprised into mini-tablets by direct compression.

Once a plurality of mini-tablets is prepared, the mini-tablets may be filled into a gelatin capsule.

In certain embodiments, the mini-tablet comprises an opioid agonist (e.g., oxycodone or a salt thereof).

In certain embodiments, a mini-tablet comprises a core and a layer comprising an active agent and a tonicity-increasing agent. If the abuser tries to dissolve the active agent containing layer, the tonicity-increasing agent will be released and produce a hypertonic solution. The abuser will therefore experience pain at the injection site. A tonicity-increasing agent may also be included in a separate layer of a mini-tablet, rather than the layer comprising the active agent.

A mini-tablet may also include one or more additional abuse-deterrent agents described above to further increase abuse deterrence of the dosage form.

In the event that the mini-tablets would be crushed the mini-tablets may include a gelling agent described above (e.g., polyethylene oxide, hydroxypropyl methyl cellulose, hydroxypropyl cellulose, etc.) which would create a viscous solution upon addition of water, impending syringe ability.

Osmotic Dosage Forms

Sustained release dosage forms according to the present invention may also be prepared as osmotic dosage formulations. The osmotic dosage form preferably include a bilayer core comprising (i) a drug layer containing an active agent susceptible to abuse and a tonicity-increasing agent, and (ii) a delivery or push layer comprising an osmopolymer and/or an osmogent, wherein the bilayer core is surrounded by a semipermeable wall and has at least one passageway disposed therein, and the tonicity-increasing agent is released from the osmotic dosage form along with the active agent susceptible to abuse when the dosage form is placed in 10 ml or from about 2 ml to about 5 ml of distilled water. The osmogent may comprise a substance which is the same or different than the substance comprising the tonicity-increasing agent and will be retained in the dosage form and exposed to distilled water when the dosage form is placed intact in 10 ml or from about 2 ml to about 5 ml of distilled water.

The expression "passageway" as used for the purpose of this invention, includes aperture, orifice, bore, pore, porous element through which the active agent can be pumped, diffuse or migrate through a fiber, capillary tube, porous overlay, porous insert, microporous member, or porous composition. The passageway can also include a compound that erodes or is leached from the wall in the fluid environment of use to produce at least one passageway. Representative compounds for forming a passageway include erodible poly(glycolic) acid, or poly(lactic) acid in the wall; a gelatinous filament; a water-removable poly(vinyl alcohol); leachable compounds such as fluid-removable pore-forming polysaccharides, acids, salts or oxides. A passageway can be formed by leaching a compound from the wall, such as sorbitol, sucrose, lactose, maltose, or fructose, to form a sustained-release dimensional pore-passageway. The passageway can have any shape, such as round, triangular, square and elliptical, for assisting in the sustained metered release of the active agent from the dosage form. The dosage form can be manufactured with one or more passageways in spaced-apart relation on one or more surfaces of the dosage form. A passageway and equipment for forming a passageway are described in U.S. Pat. Nos. 3,845,770; 3,916,899; 4,063,064 and 4,088,864, herein incorporated by reference. Passageways comprising sustained-release dimensions sized, shaped and adapted as a releasing-pore formed by aqueous leaching to provide a releasing-pore of a sustained-release rate are described in U.S. Pat. Nos. 4,200,098 and 4,285,987, herein incorporated by reference.

In certain embodiments, the bilayer core comprises a drug layer with opioid analgesic and the tonicity increasing agent and a displacement or push layer containing an osmopolymer and, optionally, one or more additional abuse-deterrent agents. The additional abuse-deterrent agent(s) may optionally be included in the drug layer instead of or in addition to being included in the push layer. In certain embodiments, the drug layer may also comprise at least one polymer hydrogel. The polymer hydrogel may have an average molecular weight of between about 500 and about 6,000,000. Examples of polymer hydrogels include but are not limited to a maltodextrin polymer comprising the formula $(C_6H_{12}O_5)_n H_2O$, wherein n is from 3 to 7,500, and the maltodextrin polymer comprises a 500 to 1,250,000 number-average molecular weight; a poly(alkylene oxide) represented by, e.g., a poly(ethylene oxide) and a poly(propylene oxide) having a 50,000 to 750,000 weight-average molecular weight, and more specifically represented by a poly(ethylene oxide) of at least one of 100,000, 200,000, 300,000 or 400,000 weight-average molecular weights; an alkali carboxyalkylcellulose, wherein the alkali is sodium or potassium, the alkyl is methyl, ethyl, propyl, or butyl of 10,000 to 175,000 weight-average molecular weight; and a copolymer of ethylene-acrylic acid, including methacrylic and ethacrylic acid of 10,000 to 500,000 number-average molecular weight.

In certain embodiments of the present invention, the delivery or push layer comprises an osmopolymer. Examples of an osmopolymer include but are not limited to a member selected from the group consisting of a polyalkylene oxide and a carboxyalkylcellulose. The polyalkylene oxide possesses a 1,000,000 to 10,000,000 average molecular weight. The polyalkylene oxide may be a member selected from the group consisting of polymethylene oxide, polyethylene oxide, polypropylene oxide, polyethylene oxide having a 1,000,000 average molecular weight, polyethylene oxide comprising a 5,000,000 average molecular weight, polyethylene oxide comprising a 7,000,000 average molecular weight, cross-linked polymethylene oxide possessing a 1,000,000 average molecular weight, and polypropylene oxide of 1,200,000 average molecular weight. Typical osmopolymer carboxyalkylcellulose comprises a member selected from the group consisting of alkali carboxyalkylcellulose, sodium carboxymethylcellulose, potassium carboxymethylcellulose, sodium carboxyethylcellulose, lithium carboxymethylcellulose, sodium carboxyethylcellulose, carboxyalkylhydroxyalkylcellulose, carboxymethylhydroxyethyl cellulose, carboxyethylhydroxyethylcellulose and carboxymethylhydroxypropylcellulose. The osmopolymers used for the displacement layer exhibit an osmotic pressure gradient across the semipermeable wall. The osmopolymers imbibe fluid into dosage form, thereby swelling and expanding as an osmotic hydrogel (also known as osmogel), whereby they push the contents of the drug layer from the osmotic dosage form.

The push layer may also include one or more osmotically effective compounds known as osmagents and as osmotically effective solutes. The compounds imbibe an environmental fluid, for example, from the gastrointestinal tract, into dosage form and contribute to the delivery kinetics of the displacement layer. Examples of osmotically active compounds comprise a member selected from the group consisting of osmotic salts and osmotic carbohydrates. Examples of specific osmagents include but are not limited to sodium chloride, potassium chloride, magnesium sulfate, lithium phosphate, lithium chloride, sodium phosphate, potassium sulfate, sodium sulfate, potassium phosphate, glucose, fructose and maltose.

The push layer may optionally include a hydroxypropylalkylcellulose possessing a 9,000 to 450,000 number-average molecular weight. The hydroxypropylalkylcellulose is represented by a member selected from the group consisting of hydroxypropylmethylcellulose, hydroxypropylethylcellulose, hydroxypropyl isopropyl cellulose, hydroxypropylbutylcellulose, and hydroxypropylpentylcellulose.

The push layer may also optionally comprise an antioxidant to inhibit the oxidation of ingredients. Some examples of antioxidants include but are not limited to a member selected from the group consisting of ascorbic acid, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiary butylphenol, alphatocopherol, and propylgallate.

In certain alternative embodiments, the dosage form comprises a substantially homogenous core comprising an active agent susceptible to abuse (e.g., opioid analgesic), a tonicity-increasing agent, and, optionally, one or more additional abuse-deterrent agents, a pharmaceutically acceptable polymer (e.g., polyethylene oxide), optionally a disintegrant (e.g., polyvinylpyrrolidone), optionally an absorption enhancer (e.g., a fatty acid, a surfactant, a chelating agent, a bile salt, etc.). The substantially homogenous core is surrounded by a semipermeable wall having a passageway (as defined above) for the release of the active agent, and the one or more aversive agents.

In certain embodiments, the semipermeable wall comprises a member selected from the group consisting of a cellulose ester polymer, a cellulose ether polymer and a cellulose ester-ether polymer. Representative wall polymers comprise a member selected from the group consisting of cellulose acylate, cellulose diacylate, cellulose triacylate, cellulose acetate, cellulose diacetate, cellulose triacetate, mono-, di- and tricellulose alkenylates, and mono-, di- and tricellulose alkinylates. The poly(cellulose) used for the present invention comprises a number-average molecular weight of 20,000 to 7,500,000.

Additional semipermeable polymers for the purpose of this invention comprise acetaldehyde dimethycellulose acetate, cellulose acetate ethylcarbamate, cellulose acetate methylcarbamate, cellulose diacetate, propylcarbamate, cellulose acetate diethylaminoacetate; semipermeable polyamide; semipermeable polyurethane; semipermeable sulfonated polystyrene; semipermeable cross-linked polymer formed by the coprecipitation of a polyanion and a polycation as disclosed in U.S. Pat. Nos. 3,173,876; 3,276,586; 3,541,005; 3,541,006 and 3,546,876; semipermeable polymers as disclosed by Loeb and Sourirajan in U.S. Pat. No. 3,133,132; semipermeable crosslinked polystyrenes; semipermeable cross-linked poly(sodium styrene sulfonate); semipermeable crosslinked poly(vinylbenzyltrimethyl ammonium chloride); and semipermeable polymers possessing a fluid permeability of $2.5 \times 10^8$ to $2.5 \times 10^2$ (cm$^2$/hr·atm) expressed per atmosphere of hydrostatic or osmotic pressure difference across the semipermeable wall. Other polymers useful in the present invention are known in the art in U.S. Pat. Nos. 3,845,770; 3,916,899 and 4,160,020; and in Handbook of Common Polymers, Scott, J. R. and W. J. Roff, 1971, CRC Press, Cleveland, Ohio, herein incorporated by reference.

In certain embodiments, the semipermeable wall is non-toxic, inert, and it maintains its physical and chemical integrity during the dispensing life of the active agent.

Transdermal Delivery Systems

The formulations of the present invention may be formulated as transdermal delivery systems, such as transdermal patches. In certain embodiments of the present invention, a transdermal patch comprises an active agent susceptible to abuse contained in a reservoir or a matrix, and an adhesive which allows the transdermal device to adhere to the skin, allowing the passage of the active agent from the transdermal device through the skin of the patient, and with the inclusion of a tonicity-increasing agent as disclosed herein that is not releasable when the dosage form is applied to the skin of a mammal but which is releasable when the dosage form is tampered with and/or applied to an oral mucosal membrane of the mammal.

In certain embodiments, the transdermal dosage form used in accordance with the invention contains a biologically acceptable polymer matrix layer. Generally, the polymers used to form the biologically acceptable polymer matrix are those capable of forming a matrix through which pharmaceuticals can pass at a controlled rate.

A non-limiting list of exemplary materials for inclusion in the polymer matrix includes polyethylene, polypropylene, ethylene/propylene copolymers, ethylene/ethylacrylate copolymers, ethylene vinyl acetate copolymers, silicones, rubber, rubber-like synthetic homo-, co- or block polymers, polyacrylic esters and the copolymers thereof, polyurethanes, polyisobutylene, chlorinated polyethylene, polyvinylchloride, vinyl chloride-vinyl acetate copolymer, polymethacrylate polymer (hydrogel), polyvinylidene chloride, poly(ethylene terephthalate), ethylene-vinyl alcohol copolymer, ethylene-vinyloxyethanol copolymer, silicones including silicone copolymers such as polysiloxane-polymethacrylate copolymers, cellulose polymers (e.g., ethyl cellulose, and cellulose esters), polycarbonates, polytetrafluoroethylene and mixtures thereof.

In certain embodiments, the materials for inclusion in the polymer matrix layer comprise silicone elastomers of the general polydimethylsiloxane structures, (e.g., silicone polymers). Preferred silicone polymers cross-link and are pharmaceutically acceptable. Other materials for inclusion in the polymer matrix layer include: silicone polymers that are cross-linkable copolymers having dimethyl and/or dimethylvinyl siloxane units which can be crosslinked using a suitable peroxide catalyst. Also preferred are those polymers consisting of block copolymers based on styrene and 1,3-dienes (particularly linear styrene-isoprene-block copolymers of styrene-butadiene-block copolymers), polyisobutylenes, polymers based on acrylate and/or methacrylate.

The polymer matrix layer may optionally include a pharmaceutically acceptable cross-linking agent. Suitable cross-linking agents include, e.g., tetrapropoxy silane.

Preferred transdermal delivery systems used in accordance with the methods of the present invention include an adhesive layer to affix the dosage form to the skin of the patient for a desired period of administration, e.g., about 10 hours to about 10 days (e.g., 7 days). If the adhesive layer of the dosage form fails to provide adhesion for the desired period of time, it is possible to maintain contact between the dosage form with the skin by, for instance, affixing the dosage form to the skin of the patient with an adhesive tape, e.g., surgical tape. It is not critical for purposes of the present invention whether adhesion of the dosage form to the skin of the patient is achieved solely by the adhesive layer of the dosage form or in connection with a peripheral adhesive source, such as surgical tape, provided that the dosage form is adhered to the patient's skin for the requisite administration period.

The adhesive layer may include any adhesive known in the art that is pharmaceutically compatible with the dosage form and preferably hypoallergenic, such as polyacrylic adhesive polymers, acrylate copolymers (e.g., polyacrylate) and polyisobutylene adhesive polymers.

In certain embodiments, the adhesive is a pressure-sensitive contact adhesive, which is preferably hypoallergenic.

The transdermal dosage forms which can be used in accordance with the present invention may optionally include a permeation enhancing agent. Permeation enhancing agents are compounds which promote penetration and/or absorption of the active agent into the blood stream of the patient. A non-limiting list of permeation enhancing agents includes polyethylene glycols, surfactants, and the like.

In certain embodiments, a transdermal dosage form which may be used in accordance with the present invention includes a non-permeable backing layer made, for example, of polyester; an adhesive layer made, for example of a polyacrylate; and a matrix containing the active agent and other desirable pharmaceutical aids such as softeners, permeability enhancers, viscosity agents and the like.

The active agent may be included in the device in a drug reservoir, drug matrix or drug/adhesive layer.

The tonicity-increasing agent may be included in the device in a drug reservoir, drug matrix or drug/adhesive layer.

A transdermal delivery system in accordance with the present invention may further comprise a softening agent. Suitable softening agents include, e.g., higher alcohols such as dodecanol, undecanol, octanol, esters of carboxylic acids, wherein the alcohol component may also be a polyethoxylated alcohol, diesters of dicarboxylic acids, such as di-n-butyladiapate, and triglycerides particularly medium-chain triglycerides of the caprylic/capric acids or coconut oil, have proved to be particularly suitable. Further examples of suitable softeners are multivalent alcohols, for example, levulinic acid, cocprylic acids glycerol and 1,2-propanediol which can also be etherified by polyethylene glycols.

In certain embodiments, the transdermal dosage form includes a removable protective layer. The removable protective layer is removed prior to application, and consists of the materials used for the production of the backing layer described above provided that they are rendered removable, for example, by a silicone treatment. Other removable protective layers, for example, are polyltetra-fluoroethylene, treated paper, allophane, polyvinyl chloride, and the like. Generally, the removable protective layer is in contact with the adhesive layer and provides a convenient means of maintaining the integrity of the adhesive layer until the desired time of application.

Transdermal delivery system providing a controlled-release of active agent susceptible to abuse (i.e., an opioid agonists) are known. For example, Duragesic® patch (commercially available from Janssen Pharmaceutical) contains an opioid agonist (fentanyl) and is said to provide adequate analgesia for up to 48 to 72 hours (2 to 3 days). This formulation can be reformulated with a tonicity-increasing agent(s) described herein to render the transdermal delivery system abuse-deterrent as described herein.

There are several types of transdermal formulations of buprenorphine reported in the literature. See, for example, U.S. Pat. No. 5,240,711 (Hille et al.), U.S. Pat. No. 5,225,199 (Hidaka et al.), U.S. Pat. No. 5,069,909 (Sharma et al.), U.S. Pat. No. 4,806,341 (Chien et al.), and U.S. Pat. No. 5,026,556 (Drust et al.), all of which are hereby incorporated by reference. These transdermal devices can also be reformulated with the tonicity-increasing agent(s) as described herein.

The transdermal delivery system used in the present invention may also be prepared by including the tonicity-increasing agent(s) in the transdermal delivery systems described in U.S. Pat. No. 5,069,909 (Sharma et al.), hereby incorporated by reference. This patent describes a laminated composite for administering buprenorphine transdermally to treat pain. The transdermal delivery system used in the present invention may also be prepared by including the tonicity-increasing agent(s) in the transdermal delivery systems described in U.S. Pat. No. 4,806,341 (Chien et al.), hereby incorporated by reference. This patent describes a transdermal morphinan narcotic analgesic or antagonist (including buprenorphine) pharmaceutical polymer matrix dosage unit having a backing layer which is substantially impervious to the buprenorphine, and a polymer matrix disc layer which is adhered to the backing layer and which has microdispensed therein effective dosage amounts of the buprenorphine.

The transdermal delivery system used in the present invention may also be prepared by including the tonicity-increasing agent(s) in the transdermal delivery systems described in U.S. Pat. No. 5,026,556 (Drust et al.), hereby incorporated by reference. Therein, compositions for the transdermal delivery of buprenorphine comprise buprenorphine in a carrier of a polar solvent material selected from the group consisting of $C_3$-$C_4$ diols, $C_3$-$C_6$ triols, and mixtures thereof, and a polar lipid material selected from the group consisting of fatty alcohol esters, fatty acid esters, and mixtures thereof, wherein the polar solvent material and the lipid material are present in a weight ratio of solvent material:lipid material of from 60:40 to about 99:1.

The transdermal delivery system used in the present invention may also be prepared in including a tonicity-increasing agent(s) in the transdermal delivery systems described in U.S. Pat. No. 4,588,580 (Gale, et. al.), hereby incorporated by reference. That system comprises a reservoir for the drug having a skin proximal, material releasing surface area in the range of about 5-100 $cm^2$ and containing between 0.1 and 50% by weight of a skin permeable form of the buprenorphine. The reservoir contains an aqueous gel comprising up to about 47-95% ethanol, 1-10% gelling agent, 0.1-10% buprenorphine, and release rate controlling means disposed in the flow path of the drug to the skin which limits the flux of the buprenorphine from the system through the skin.

The transdermal delivery system used in the present invention may also be prepared by including a tonicity-increasing agent in the transdermal delivery systems described in PCT/US01/04347 to Oshlack et al.

The present invention is contemplated to encompass all transdermal formulations, e.g., the technologies described above, with the inclusion of a tonicity-increasing agent, such that the dosage form deters abuse of the active agent therein.

The tonicity-increasing agent in a sequestered form may be included in the formulations described in U.S. Pat. No. 5,149,538 to Granger, hereby incorporated by reference. In certain embodiments, the tonicity-increasing agent and the active agent susceptible to abuse can be separated from each other by a layer which becomes disrupted when the dosage form is tampered with, thereby mixing the tonicity-increasing agent with the active agent susceptible to abuse. In certain embodiments, a combination of both systems can be used.

Suppositories

The controlled release formulations of the present invention may be formulated as a pharmaceutical suppository for rectal or vaginal administration comprising an active agent susceptible to abuse (e.g., an opioid analgesic) and a tonicity-increasing agent in a suppository vehicle (base).

The tonicity-increasing agent may be in a sequestered form or in a releasable form.

In the embodiments where a releasable form of the tonicity-increasing agent is used, the amount of the tonicity-increasing agent included in the suppository is such that it will be insufficient to form a hypertonic solution, suspension or gel when only one suppository is administered but will form a hypertonic solution, suspension or gel when at least two or three suppositories are administered at the same time.

The suppository base chosen should be compatible with the active agent(s) of the present invention. Further, the suppository base is preferably non-toxic and non-irritating to mucous membranes when administered as intended, melts or dissolves in rectal fluids, and is stable during storage.

In certain preferred embodiments of the present invention for both water-soluble and water-insoluble drugs, the suppository base comprises a fatty acid wax selected from the group consisting of mono-, di- and triglycerides of saturated, natural fatty acids of the chain length $C_{12}$ to $C_{18}$.

In preparing the suppositories of the present invention other excipients may be used. For example, a wax may be used to form the proper shape for administration via the rectal route. This system can also be used without wax, but with the addition of diluent filled in a gelatin capsule for both rectal and oral administration.

Examples of suitable commercially available mono-, di- and triglycerides include saturated natural fatty acids of the 12-18 carbon atom chain sold under the trade name Novata™ (types AB, AB, B, BC, BD, BBC, E, BCF, C, D and 299), manufactured by Henkel, and Witepsol™ (types H5, H12, H15, H175, H185, H19, H32, H35, H39, H42, W25, W31, W35, W45, S55, S58, E75, E76 and E85), manufactured by Dynamit Nobel.

Other pharmaceutically acceptable suppository bases may be substituted in whole or in part for the above-mentioned mono-, di- and triglycerides. The amount of base in the suppository is determined by the size (i.e. actual weight) of the dosage form, the amount of base (e.g., alginate) and drug used. Generally, the amount of suppository base is from about 20 percent to about 90 percent by weight of the total weight of the suppository. Preferably, the amount of base in the suppository is from about 65 percent to about 80 percent, by weight of the total weight of the suppository.

DETAILED DESCRIPTION OF THE PREFERRED EMBODIMENTS

Example 1

To determine whether mixtures formed by crushing tablets formulated prior to the present invention and mixing the crushed tablets with 3 mL or 5 mL of distilled water are hypertonic, a 30 mg Roxicodone® tablet[1] (oxycodone hydrochloride tablets USP) was crushed with a mortar and pestle to a powder. The powder was then transferred to a scintillation vial, 3 mL of distilled water was added to the scintillation vial, and 0.25 ml of the resulting mixture was drawn from the scintillation vial for osmolality testing. The procedure was then repeated using 5 mL, rather than 3 mL, of distilled water. The osmolalities of the resulting mixtures were measured twice using Osmometer Model 3250 manufactured by Advanced Instruments, Inc. The following results were obtained:

[1] 30 mg Roxicodone® tablet (oxycodone hydrochloride tablets USP) contains the following inactive ingredients: microcrystalline cellulose; sodium starch glycolate; corn starch; lactose; stearic acid; and FD&C Blue No. 2.

|  | 3 mL Dilution | 5 mL Dilution |
| --- | --- | --- |
| Measurement 1 | 79 mOsm | 44 mOsm |
| Measurement 2 | 83 mOsm | 44 mOsm |

It was concluded that mixtures formed by crushing tablets formulated prior to the present invention (i.e., Roxicodone® tablet (oxycodone hydrochloride tablets USP)) and mixing the crushed tablets with 3 mL or 5 mL of distilled water are not hypertonic. Intravenous injections of these mixtures are not therefore expected to cause pain and burning at the injection cite.

Example 2 (prophetic)

1. A sustained release tablet with the following formulation is prepared using conventional techniques:

| Component | Amount (weight %) |
|---|---|
| Oxycodone HCl | 20% |
| Sodium Bicarbonate | 20% |
| Microcrystalline Cellulose | 29% |
| Magnesium Stearate | 1% |
| Polyethylene Oxide | 30% |

2. The tablet is crushed to a powder and the powder is dissolved in 10 ml of distilled water.
3. The osmolality of the resulting solution is measured, to confirm that the solution is hypertonic, as compared to 0.9% sodium chloride distilled water solution.
4. If the measured osmolality is not hypertonic, an additional amount of sodium bicarbonate is added to the tablet formulation so that the resulting solution tested as above will be hypertonic.

Example 3 (prophetic)

1. A sustained release mini-tablet with the following formulation is prepared using conventional techniques:

| Component | Amount (weight %) |
|---|---|
| Oxycodone HCl | 10% |
| Sodium Bicarbonate | 20% |
| Microcrystalline Cellulose | 67% |
| Magnesium Stearate | 1% |
| Polyethylene Oxide | 2% |

2. Five mini-tablets are crushed to a powder and the powder is dissolved in 10 ml of distilled water.
3. The osmolality of the resulting solution is measured, to confirm that the solution is hypertonic, as compared to 0.9% sodium chloride distilled water solution.
4. If the measured osmolality is not hypertonic, an additional amount of sodium bicarbonate is added to the mini-tablet formulation so that the resulting solution tested as above will be hypertonic.

Example 4 (prophetic)

1. An immediate release tablet with the following formulation is prepared using conventional techniques:

| Component | Amount (weight %) |
|---|---|
| Oxycodone HCl | 15% |
| Sodium Bicarbonate | 20% |
| Microcrystalline Cellulose | 62% |
| Magnesium Stearate | 1% |
| Polyethylene Oxide | 2% |

2. The tablet is crushed to a powder and the powder is dissolved in 10 ml of distilled water.
3. The osmolality of the resulting solution is measured, to confirm that the solution is hypertonic, as compared to 0.9% sodium chloride distilled water solution.
4. If the measured osmolality is not hypertonic, an additional amount of sodium bicarbonate is added to the tablet so that the resulting solution tested as above will be hypertonic.

Example 5

Five compressed tablets, each weighing about 400 mg and containing 5 mg of hydrocodone bitartrate, were prepared from each of the following formulation blends:

| Ingredient | C1 (mg) | C2 (mg) | D3 (mg) | D4 (mg) |
|---|---|---|---|---|
| Hydrocodone Bitartrate | 25 | 25 | 25 | 25 |
| MCC | 200 | 200 | 200 | 200 |
| NaCl | 200 | 400 | | |
| $K_2HPO_4$ | | | 200 | 400 |
| Mag. Stearate | 10 | 10 | 10 | 10 |
| Dextrose | 1565 | 1365 | 1565 | 1365 |

In these tablets, dextrose, sodium chloride and potassium phosphate dibasic were used as tonicity-increasing agents.

To determine whether the mixtures (i.e., solutions, suspensions or gels) formed by crushing these tablets and mixing the crushed tablets with 3 mL or 5 mL of distilled water are hypertonic, one tablet of each formulation was crushed with a mortar and pestle. The crushed tablet was then transferred to a scintillation vial, 3 mL of distilled water was added to the scintillation vial, and 0.25 ml of the resulting mixture was drawn for osmolality testing. The procedure was then repeated using 5 mL, rather than 3 mL, of distilled water. The osmolality of the resulting mixtures was measured using Osmometer Model 3250 manufactured by Advanced Instruments, Inc. The following results were obtained:

| Sample ID | 3 mL dilution (mOsmol) | 5 mL dilution (mOsmol) |
|---|---|---|
| C1 | 1003 | 618 |
| C2 | 1391 | 884 |
| D3 | 641 | 457 |
| D4 | 801 | 473 |

It was concluded that tablets of all four formulations when crushed and mixed with 3 mL or 5 mL of distilled water formed mixtures (i.e., solutions, suspensions or gels) which were hypertonic. Intravenous injections of these mixtures are expected to cause pain and burning at the injection cites.

As a control, the osmolality of hydrocodone bitartrate solution, 1 mg/ml, which did not contain any dextrose, sodium chloride and potassium phosphate dibasic, was measured and shown to be 4 mOsmol. An intravenous injection of this solution is not expected to cause pain and burning at the injection cite.

Example 6

Five compressed tablets, each weighing about 400 mg and containing 5 mg of oxycodone HCl, were prepared from each of the following formulation blends:

| Ingredient | A1 (mg) | A2 (mg) | B1 (mg) | B2 (mg) |
|---|---|---|---|---|
| Oxycodone HCl | 25 | 25 | 25 | 25 |
| MCC | 200 | 200 | 200 | 200 |
| NaCl | 200 | 400 | | |
| $K_2HPO_4$ | | | 200 | 400 |

| Ingredient | A1 (mg) | A2 (mg) | B1 (mg) | B2 (mg) |
| --- | --- | --- | --- | --- |
| Mag. Stearate | 10 | 10 | 10 | 10 |
| Dextrose | 1565 | 1365 | 1565 | 1365 |

In these tablets, dextrose, sodium chloride and potassium phosphate dibasic were used as tonicity-increasing agents.

To determine whether the mixtures (i.e., solutions, suspensions or gels) formed by crushing these tablets and mixing the crushed tablets with 3 mL or 5 mL of distilled water are hypertonic, one tablet of each formulation was crushed with a mortar and pestle. The crushed tablet was then transferred to a scintillation vial, 3 mL of distilled water was added to the scintillation vial, and 0.25 ml of the resulting mixture was drawn for osmolality testing. The procedure was then repeated using 5 mL, rather than 3 mL, of distilled water. The osmolality of the resulting mixtures was measured using Osmometer Model 3250 manufactured by Advanced Instruments, Inc. The following results were obtained:

| Sample ID | 3 mL dilution (mOsmol) | 5 mL dilution (mOsmol) |
| --- | --- | --- |
| A1 | 1098 | 621 |
| A2 | 1315 | 668 |
| A3 | 707 | 462 |
| A4 | 803 | 499 |

It was concluded, that tablets of all four formulations when crushed and mixed with 3 mL or 5 mL of distilled water formed mixtures (i.e., solutions, suspensions or gels) which were hypertonic. Intravenous injections of these mixtures are expected to cause pain and burning at the injection cites.

Example 7

Compressed tablets, each containing 5 mg of oxycodone HCl, were prepared from each of the following formulation blends:

| Ingredient | Blend 1 (mg) | Blend 2 (mg) |
| --- | --- | --- |
| Oxycodone HCl | 25 | 25 |
| MCC | 1965 | 200 |
| Mag. Stearate | 10 | 10 |
| Dextrose | 0 | 1765 |

As compared to the formulation of Blend 1, the formulation of Blend 2 included dextrose as a tonicity increasing agent.

To determine whether the mixtures (i.e., solutions, suspensions or gels) formed by crushing these tablets and mixing the crushed tablets with 3 mL or 5 mL of distilled water are hypertonic, one tablet from each blend was crushed with a mortar and pestle to a powder. The powder was then transferred to a scintillation vial, 3 mL of distilled water was added to the scintillation vial, and 0.25 ml of the resulting mixture was drawn for osmolality testing. The procedure was then repeated using 5 mL, rather than 3 mL, of distilled water. The osmolality of the resulting mixtures was measured twice using Osmometer Model 3250 manufactured by Advanced Instruments, Inc. The following results were obtained:

|  | 3 mL Dilution | 5 mL Dilution |
| --- | --- | --- |
| Blend 1 |  |  |
| Measurement 1 | 9 mOsm | 5 mOsm |
| Measurement 2 | 9 mOsm | 5 mOsm |
| Blend 2 |  |  |
| Measurement 1 | 641 mOsm | 386 mOsm |
| Measurement 2 | 656 mOsm | 388 mOsm |

It was concluded that tablets compressed from Blend 1, the blend that did not include dextrose as a tonicity increasing agent, when crushed and mixed with 3 mL or 5 mL of distilled water did not form mixtures (i.e., solutions, suspensions or gels) which are hypertonic. Intravenous injections of these mixtures are not expected to cause pain and burning at the injection cites.

Conversely, the tablets compressed from Blend 2, the blend that included dextrose as a tonicity increasing agent, when crushed and mixed with 3 mL or 5 mL of distilled water formed mixtures (i.e., solutions, suspensions or gels) which are hypertonic. Intravenous injections of these mixtures are expected to cause pain and burning at the injection cites.

Tablets prepared from Blend 2 therefore have a lower abuse potential than tablets prepared from Blend 1.

Example 8

Compressed tablets, each containing 5 mg of hydrocodone bitartrate, were prepared from each of the following formulation blends:

| Ingredient | Blend 3 (mg) | Blend 4 (mg) |
| --- | --- | --- |
| Hydrocodone Bitartrate | 25 | 25 |
| MCC | 1965 | 200 |
| Mag. Stearate | 10 | 10 |
| Dextrose | 0 | 1765 |

As compared to the formulation of Blend 3, the formulation of Blend 4 included dextrose as a tonicity increasing agent.

To determine whether the mixtures (i.e., solutions, suspensions or gels) formed by crushing these tablets and mixing the crushed tablets with 3 mL or 5 mL of distilled water are hypertonic, one tablet from each blend was crushed with a mortar and pestle to a powder. The powder was then transferred to a scintillation vial, 3 mL of distilled water was added to the scintillation vial, and 0.25 ml of the resulting mixture was drawn for osmolality testing. The procedure was then repeated using 5 mL, rather than 3 mL, of distilled water. The osmolality of the resulting mixtures was measured twice using Osmometer Model 3250 manufactured by Advanced Instruments, Inc. The following results were obtained:

|  | 3 mL Dilution | 5 mL Dilution |
| --- | --- | --- |
| Blend 3 | | |
| Measurement 1 | 9 mOsm | 5 mOsm |
| Measurement 2 | 9 mOsm | 4 mOsm |
| Blend 4 | | |
| Measurement 1 | 653 mOsm | 383 mOsm |
| Measurement 2 | 650 mOsm | 383 mOsm |

It was concluded that tablets compressed from Blend 3, the blend that did not include dextrose as a tonicity increasing agent, when crushed and mixed with 3 mL or 5 mL of distilled water did not form mixtures (i.e., solutions, suspensions or gels) which are hypertonic. Intravenous injections of these mixtures are not expected to cause pain and burning at the injection cites.

Conversely, the tablets compressed from Blend 4, the blend that included dextrose as a tonicity increasing agent, when crushed and mixed with 3 mL or 5 mL of distilled water formed mixtures (i.e., solutions, suspensions or gels) which are hypertonic. Intravenous injections of these mixtures are expected to cause pain and burning at the injection cites.

Tablets prepared from Blend 2 therefore have a lower abuse potential than tablets prepared from Blend 1.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

What is claimed is:

1. An abuse-deterrent dosage form comprising an active agent susceptible to abuse and a tonicity-increasing agent, wherein the tonicity-increasing agent is in an effective amount to provide a hypertonic solution, suspension or gel comprising the active agent upon contact of the dosage form with from 2 ml to 5 ml of a solvent, the hypertonic solution, suspension or gel has an osmotic pressure of from about 380 mOsmol/L to about 10000 mOsmol/L, a viscosity of less than about 8 cP and is sufficiently hypertonic to deter abuse, the abuse-deterrent dosage form is an abuse-deterrent transdermal dosage form, the active agent susceptible to abuse is an opioid agonist, the solvent comprises water, saliva and/or nasal secretions, and the tonicity-increasing agent is the only abuse-deterrent agent in the dosage form.

2. The dosage form of claim 1, wherein the tonicity-increasing agent is sequestered in one or more particles.

3. The dosage form of claim 2, wherein at least one of said particles comprises the tonicity-increasing agent dispersed in a hydrophobic material.

4. The dosage form of claim 2, wherein at least one of said particles comprises the tonicity-increasing agent coated with a hydrophobic material.

5. The dosage form of claim 2, wherein at least one of said particles comprises the tonicity-increasing agent dispersed in a first hydrophobic material and coated with a second hydrophobic material, and the hydrophobic materials are independently selected from the group consisting of (i) an alkylcellulose; (ii) an acrylic polymer; or (iii) mixtures thereof.

6. The dosage form of claim 1, which releases the active agent at a controlled release rate for a time period of from about 30 minutes to about 30 hours.

7. The dosage form of claim 1, wherein the dosage form releases at least 50% of the active agent and the tonicity-increasing agent within 30 minutes of placement of the dosage form in 900 ml of water.

8. The dosage form of claim 1, wherein the opioid agonist is selected from the group consisting of oxycodone, hydrocodone, hydromorphone, morphine and salts of any of the foregoing.

* * * * *